US012661520B2

(12) United States Patent
Schwemmer et al.

(10) Patent No.: US 12,661,520 B2
(45) Date of Patent: *Jun. 23, 2026

(54) MEETING BRAIN-COMPUTER INTERFACE USER PERFORMANCE EXPECTATIONS USING A DEEP NEURAL NETWORK DECODING FRAMEWORK

(71) Applicant: Battelle Memorial Institute, Columbus, OH (US)

(72) Inventors: Michael A. Schwemmer, Columbus, OH (US); David A. Friedenberg, Worthington, OH (US); Nicholas D. Skomrock, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/223,807

(22) Filed: Jul. 19, 2023

(65) Prior Publication Data

US 2023/0364432 A1 Nov. 16, 2023

Related U.S. Application Data

(63) Continuation of application No. 16/811,702, filed on Mar. 6, 2020, now Pat. No. 11,752,349.

(Continued)

(51) Int. Cl.
*A61N 1/372* (2006.01)
*A61N 1/36* (2006.01)
(Continued)

(52) U.S. Cl.
CPC ..... *A61N 1/37247* (2013.01); *A61N 1/36003* (2013.01); *B25J 13/06* (2013.01);
(Continued)

(58) Field of Classification Search
None
See application file for complete search history.

(56) References Cited

U.S. PATENT DOCUMENTS

| | | | |
|---|---|---|---|
| 7,826,894 | B2 | 11/2010 | Musallam et al. |
| 2002/0016638 | A1 | 2/2002 | Mitra et al. |

(Continued)

OTHER PUBLICATIONS

Sussillo, David et al, Making brain-machine interfaces robust to future neural variability, Nature Communications, Dec. 13, 2016, pp. 1-12, Nature Communications.

(Continued)

*Primary Examiner* — Raymond L Nimox
(74) *Attorney, Agent, or Firm* — Lippes Mathias LLP

(57) ABSTRACT

A brain-computer interface (BCI) includes a multichannel stimulator and a decoder. The multichannel stimulator is operatively connected to deliver stimulation pulses to a functional electrical stimulation (FES) device to control delivery of FES to an anatomical region. The decoder is operatively connected to receive at least one neural signal from at least one electrode operatively connected with a motor cortex. The decoder controls the multichannel stimulator based on the received at least one neural signal. The decoder comprises a computer programmed to process the received at least one neural signal using a deep neural network. The decoder may include a long short-term memory (LSTM) layer outputting to a convolutional layer in turn outputting to at least one fully connected neural network layer. The decoder may be updated by unsupervised updating. The decoder may be extended to include additional functions by transfer learning.

17 Claims, 15 Drawing Sheets

Related U.S. Application Data

(60) Provisional application No. 62/815,626, filed on Mar. 8, 2019, provisional application No. 62/815,640, filed on Mar. 8, 2019.

(51) Int. Cl.

| | |
|---|---|
| *B25J 13/06* | (2006.01) |
| *G05B 13/02* | (2006.01) |
| *G06N 3/044* | (2023.01) |
| *G06N 3/047* | (2023.01) |
| *G06N 3/088* | (2023.01) |
| *G16H 40/67* | (2018.01) |

(52) U.S. Cl.
CPC ........... *G05B 13/027* (2013.01); *G06N 3/044* (2023.01); *G06N 3/047* (2023.01); *G06N 3/088* (2013.01); *G16H 40/67* (2018.01)

(56) References Cited

U.S. PATENT DOCUMENTS

| | | | |
|---|---|---|---|
| 2011/0307079 | A1 | 12/2011 | Oweiss et al. |
| 2014/0058528 | A1 | 2/2014 | Contreras-Vidal et al. |
| 2016/0048753 | A1 | 2/2016 | Sussillo et al. |
| 2016/0224891 | A1 | 8/2016 | Kao et al. |
| 2016/0242690 | A1 | 8/2016 | Principe et al. |
| 2018/0177619 | A1 | 6/2018 | Zhang et al. |
| 2019/0110754 | A1 | 4/2019 | Rao et al. |

| | | | | |
|---|---|---|---|---|
| 2019/0244108 | A1 * | 8/2019 | Meyerson | ............. G06N 3/044 |
| 2019/0247650 | A1 * | 8/2019 | Tran | .................... A61N 1/3704 |
| 2021/0365114 | A1 | 11/2021 | Hewage et al. | |

OTHER PUBLICATIONS

Sussillo, David et al., A recurrent neural network for closed-loop intracortical brain-machine interface decoders, Journal of Neural Engineering, Apr. 9, 2012, pp. 1-21, NIH Public Access.

Roset, Scott A. et al., An adaptive brain actuated system for augmenting rehabilitation, Neuroprosthetics, Dec. 12, 2014, pp. 1-8, vol. 8, Article 415, Frontiers in Neuroscience.

Miles, Matt, Building a better brain-computer interface, Nature Medicine, Oct. 2, 2018, pp. 1-3, Medical Xpress.

Lecun, Yann et al., Deep Learning, May 28, 2015, pp. 436-444, vol. 521, Nature Publishing Group.

Homer, Mark L. et al., Implants and Decoding for Intracortical Brain Computer Interfaces, Annu Rev Biomed Eng., Apr. 14, 2014, pp. 1-28, NIH Public Access.

Guo, Yi et al., Convolutional Networks Outperform Linear Decoders in Predicting EMG From Spinal Cord Signals, Oct. 17, 2018, pp. 1-16, vol. 12, Article 689, Frontiers in Neuroscience.

Schwemmer, Michael A. et al., Meeting brain-computer interface user performance expectations using a deep neural network decoding framework, Nov. 2018, pp. 1669-1676, vol. 24, Nature Medicine.

Skomrock, Nicholas D. et al., A Characterization of Brain-Computer Interface Performance Trade-Offs Using Support Vector Machines and Deep Neural Networks to Decode Movement Intent, Oct. 24, 2018, pp. 1-14, vol. 12, Frontiers in Neuroscience.

* cited by examiner

Response times for each participant by hand movement (mean ± s.d).

| Participant | Index extension | Index flexion | Hand close | Hand open | Wrist flexion | Wrist extension |
|---|---|---|---|---|---|---|
| Able-bodied (9) | 365 ± 85 | 399 ± 86 | 401 ± 87 | 384 ± 98 | 373 ± 80 | 387 ± 98 |
| Participant 1 Movement | 896 ± 158 | 1,128 ± 181 | 1,044 ± 183 | 1,031 ± 154 | 888 ± 150 | 957 ± 376 |
| Participant 1 Decoder | 714 ± 107 | 830 ± 241 | 982 ± 213 | 1,018 ± 194 | 745 ± 137 | 800 ± 151 |

MEETING BRAIN-COMPUTER INTERFACE USER PERFORMANCE EXPECTATIONS USING A DEEP NEURAL NETWORK DECODING FRAMEWORK

This application is a continuation of U.S. application Ser. No. 16/811,702, filed Mar. 6, 2020, which claims the benefit of provisional application No. 62/815,626 filed Mar. 8, 2019 and titled "MEETING BRAIN-COMPUTER INTERFACE USER PERFORMANCE EXPECTATIONS USING A DEEP NEURAL NETWORK DECODING FRAME-WORK". This application also claims the benefit of provisional application No. 62/815,640 filed Mar. 8, 2019 and titled "A CHARACTERIZATION OF BRAIN-COMPUTER INTERFACE PERFORMANCE TRADE-OFFS USING SUPPORT VECTOR MACHINES AND DEEP NEURAL NETWORKS TO DECODE MOVEMENT INTENT". Provisional application No. 62/815,626 filed Mar. 8, 2019 is incorporated herein by reference in its entirety. Provisional application No. 62/815,640 filed Mar. 8, 2019 is incorporated herein by reference in its entirety.

BACKGROUND

The following relates to functional electrical stimulation (FES), brain-computer interface (BCI) systems, combined BCI-FES systems, to methods employing same, and to like applications.

Brain-computer interface (BCI) systems that directly link neural activity to assistive devices have shown great promise for improving the daily lives of individuals with paralysis. Using BCIs, individuals with tetraplegia have demonstrated control of computer cursors, robotic arms, communication devices, and their own paralyzed limbs through imagined movements. In anticipation of these technologies transitioning from the laboratory setting to everyday usage, several groups have surveyed potential BCI users to identify patient priorities and desired characteristics for a clinically viable BCI. These studies revealed that potential BCI users prioritize non-invasiveness, daily set-up time/simplicity of set-up, independent operation, cost, number of functions provided, accuracy, and response time as important design characteristics, with the most desired target for BCI control being the restoration of hand and arm function. These priorities highlight some of the remaining challenges that need to be overcome for BCI technology to be translated from laboratory demonstration to clinical usage.

Certain improvements are disclosed herein.

BRIEF SUMMARY

In accordance with some illustrative embodiments disclosed herein, a brain-computer interface (BCI) comprises a multichannel stimulator and a decoder. The multichannel stimulator is operatively connected to deliver stimulation pulses to a functional electrical stimulation (FES) device to control delivery of FES to an anatomical region. The decoder is operatively connected to receive at least one neural signal from at least one electrode operatively connected with a motor cortex, and to control the multichannel stimulator based on the received at least one neural signal. The decoder suitably comprises a computer programmed to process the received at least one neural signal using a deep neural network. In some embodiments, the deep neural network comprises a long short-term memory (LSTM) layer outputting to a convolutional layer in turn outputting to at least one fully connected neural network layer. In some embodiments, the decoder generates a predicted movement of the anatomical region based on the received at least one neural signal and controls the multichannel stimulator based on the predicted movement of the anatomical region, and the computer is further programmed to perform unsupervised updating of the decoder using the at least one neural signal labeled with the predicted movement generated by the decoder as training data for the unsupervised updating.

In accordance with some illustrative embodiments disclosed herein, an assistance device is disclosed for assisting a patient having a spinal cord injury to manipulate an anatomical region that is paralyzed due to the spinal cord injury. The assistance device includes a BCI as set forth in the immediately preceding paragraph, and a functional electrical stimulation (FES) device disposed on the anatomical region and including electrodes configured to deliver FES to the anatomical region. The multichannel stimulator of the BCI is operatively connected to deliver stimulation pulses to the FES device to control delivery of FES to the anatomical region. The assistance device may further include the aforementioned at least one electrode.

In accordance with some illustrative embodiments disclosed herein, an assistance method is disclosed for assisting a patient having a spinal cord injury to manipulate an anatomical region of the patient that is paralyzed due to the spinal cord injury. The assistance method includes applying a decoder to at least one neural signal received from at least one electrode operatively connected with a motor cortex of the patient to generate a predicted movement of the anatomical region, and performing functional electrical stimulation (FES) to cause the predicted movement of the anatomical region using a multichannel stimulator that is operatively connected to deliver stimulation pulses to a functional electrical stimulation (FES) device operatively connected to the anatomical region. The decoder comprises a computer programmed to process the at least one neural signal using a deep neural network to generate the predicted movement of the anatomical region. In some embodiments, the deep neural network includes an output neural network layer having units corresponding to a set of possible intended movements plus rest, and the assistance method further comprises generating an expanded deep neural network by adding units to the output neural network layer to add additional possible intended movements, and performing transfer learning of the expanded deep neural network including a training stage in which all weights of the expanded deep neural network are fixed except the weights of the output neural network layer. In some embodiments the assistance method further includes performing unsupervised updating of the decoder using the at least one neural signal labeled with the predicted movement of the anatomical region generated by applying the decoder to the at least one neural signal.

In accordance with some illustrative embodiments disclosed herein, an assistance system comprises a brain-computer interface (BCI) and an assistive device. The BCI comprises a computer operatively connected to receive at least one neural signal from a patient and programmed to apply a decoder to the at least one neural signal to generate a predicted movement, wherein the decoder comprises a deep neural network. The BCI is operatively connected to control the assistive device to perform the predictive movement. In some illustrative embodiments, the assistive device comprises a functional electrical stimulation (FES) device, a robotic arm, a computer cursor, or a communication device. In some illustrative embodiments, the deep neural network comprises a long short-term memory (LSTM) layer outputting to a convolutional layer in turn outputting to at least one fully connected neural network layer. In some illustrative embodiments, the computer is further programmed to perform unsupervised updating of the decoder using the at least one neural signal labeled with the predicted movement generated by applying the decoder to the at least one neural signal. In some illustrative embodiments, the deep neural network includes an output neural network layer having units corresponding to a set of possible intended movements plus rest, and the computer is further programmed to: generate an expanded deep neural network by adding units to the output neural network layer to add additional possible intended movements; and perform transfer learning of the expanded deep neural network including a training stage in which all weights of the expanded deep neural network are fixed except the weights of the output neural network layer.

BRIEF DESCRIPTION OF THE DRAWINGS

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

FIG. 10 part (b) presents accuracy as a function of days since last training session. Solid lines and circles are again decoders using the boxcar filter and dashed lines with triangles are again without the boxcar filter.

4 response times for a decoder-filter combination and hand movement are represented by solid vertical lines.

Figure 12:
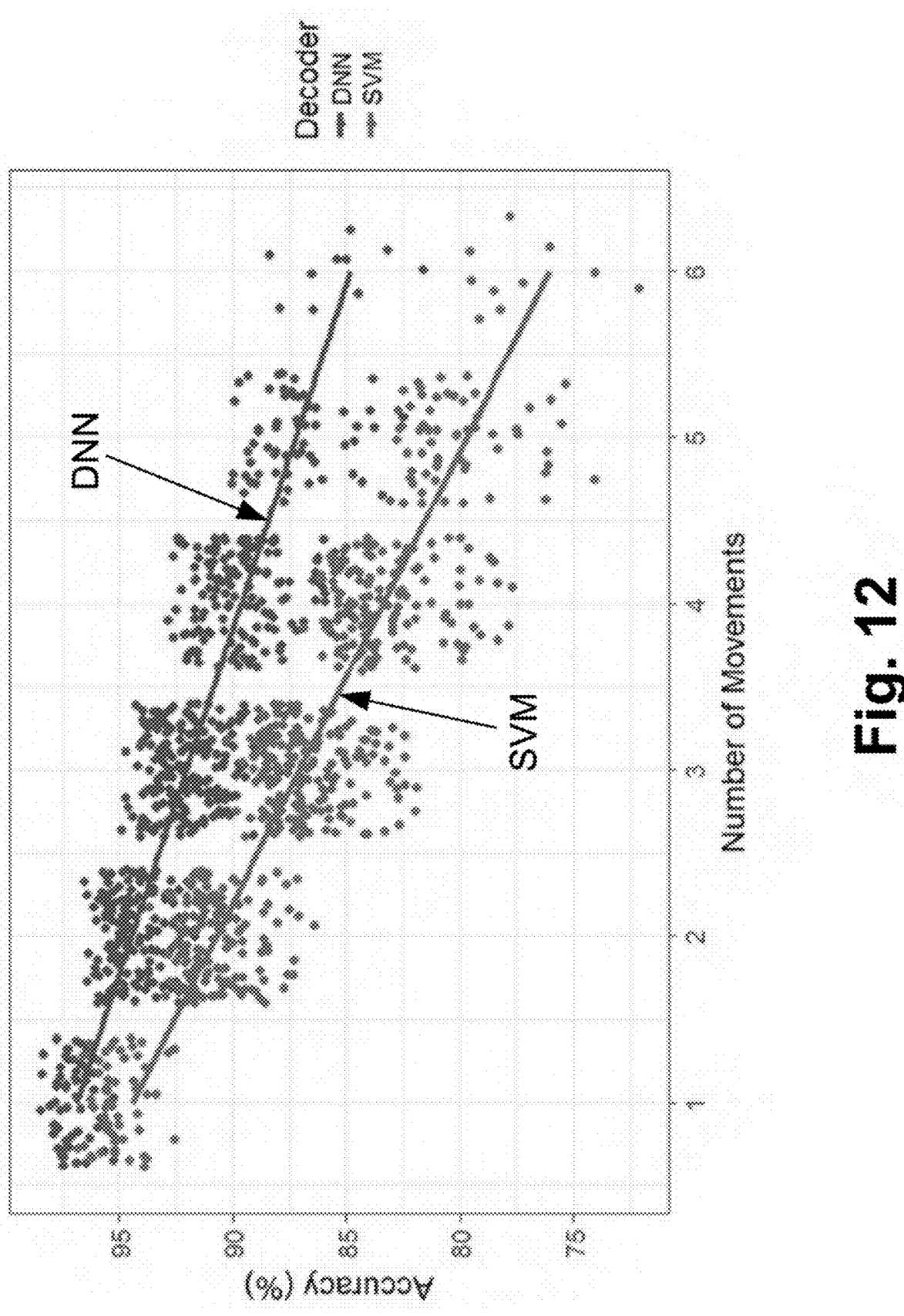

FIG. 12 presents accuracy as a function of the number of movements during an offline simulation. The accuracy across each of the testing days in the simulation. A jitter is applied for easy visualization and a linear regression model is fit to the original data.

Figure 13:
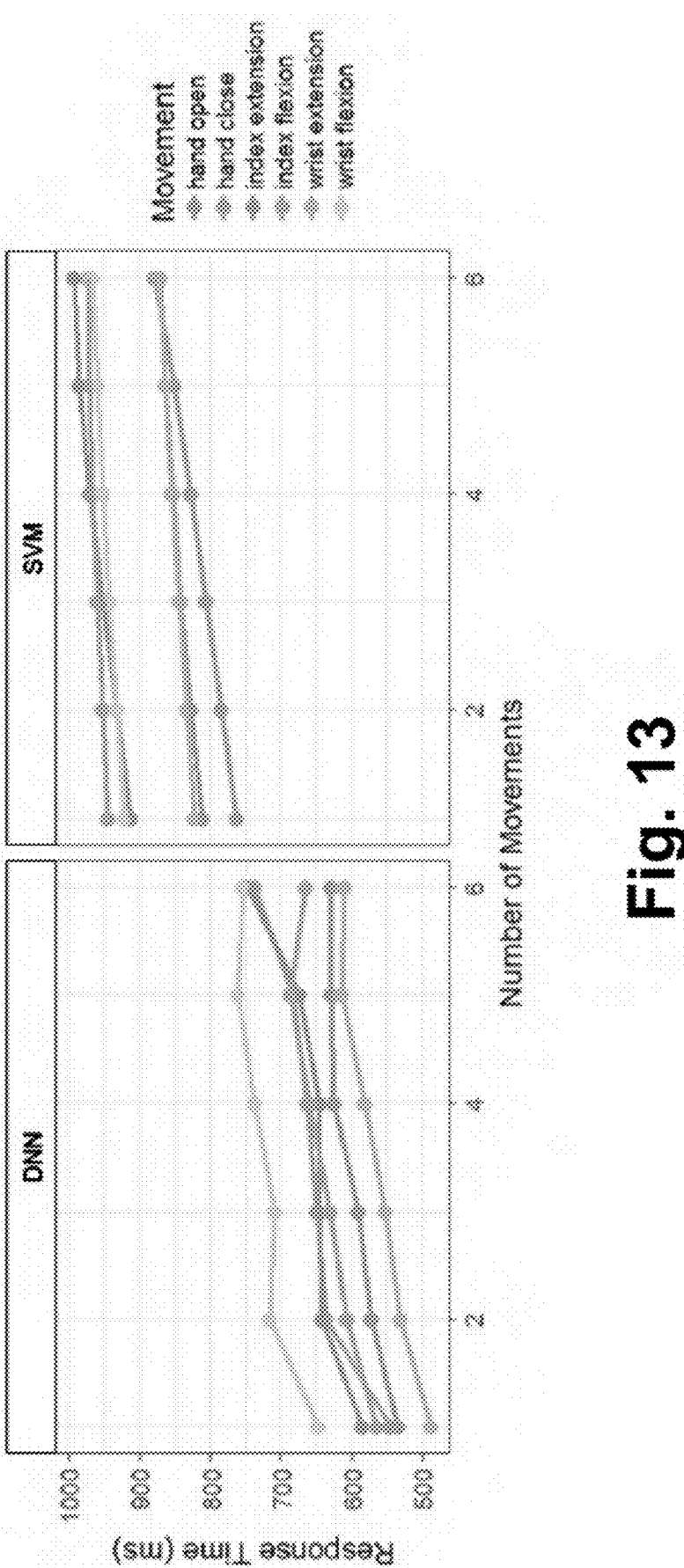

FIG. 13 presents mean response time as a function of the number of movements during the offline simulation of FIG. 12. As the number of movements increase, so does the mean response time for both model types.

Figure 14:
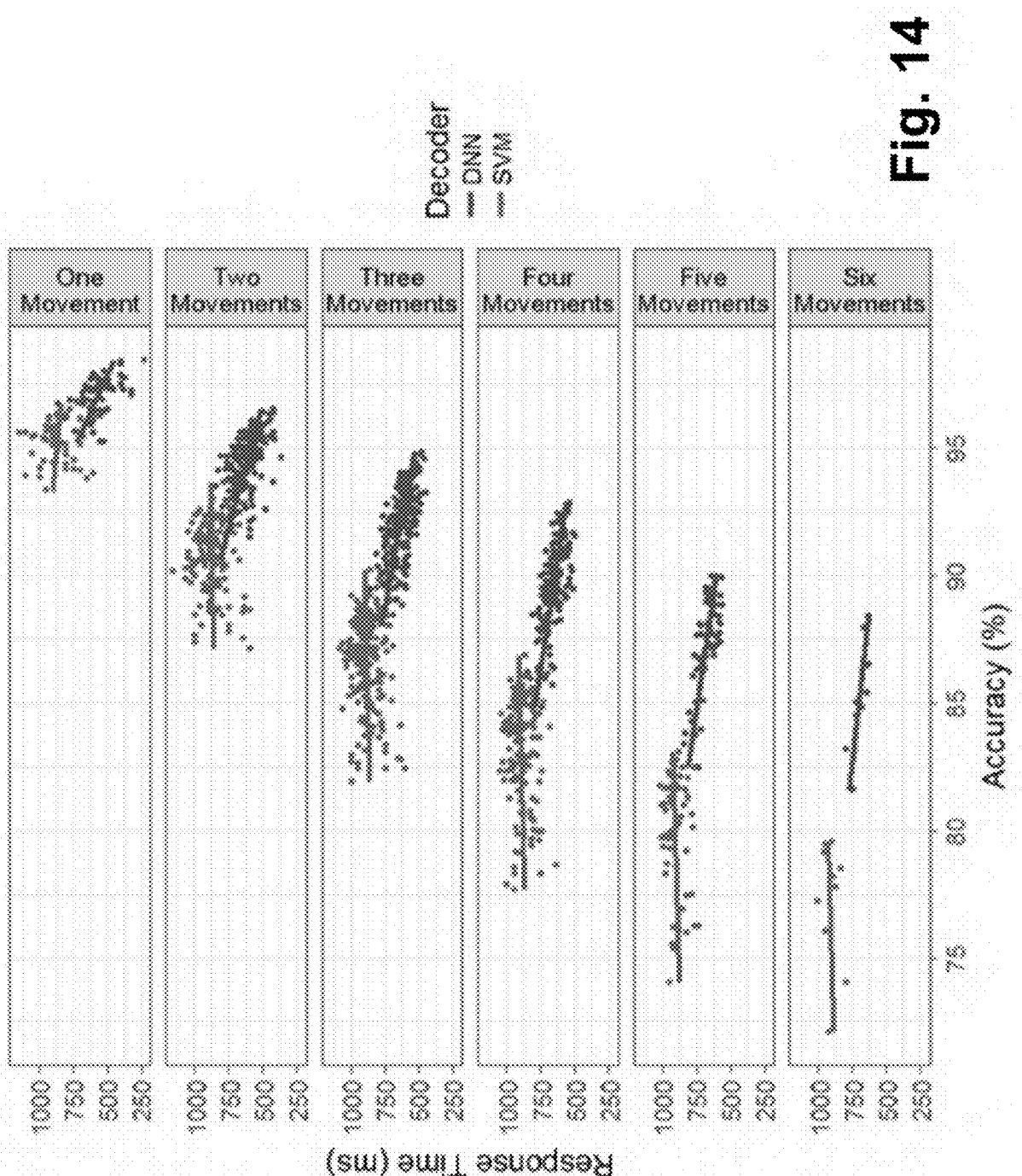

FIG. 14 presents response time as a function of accuracy for the offline simulation of FIGS. 12 and 13. For each number of hand movements in the simulation, the mean response time is plotted against the accuracy for each separate test days. The SVM is with the boxcar. Solid lines are linear regression models fit to each set of points. For the SVM, all of the models appear to be flat, allowing for large variation in accuracy while maintaining similar response times. For the DNN, the trend shows a decrease in response time with an increase in accuracy.

Figures 15, 16:
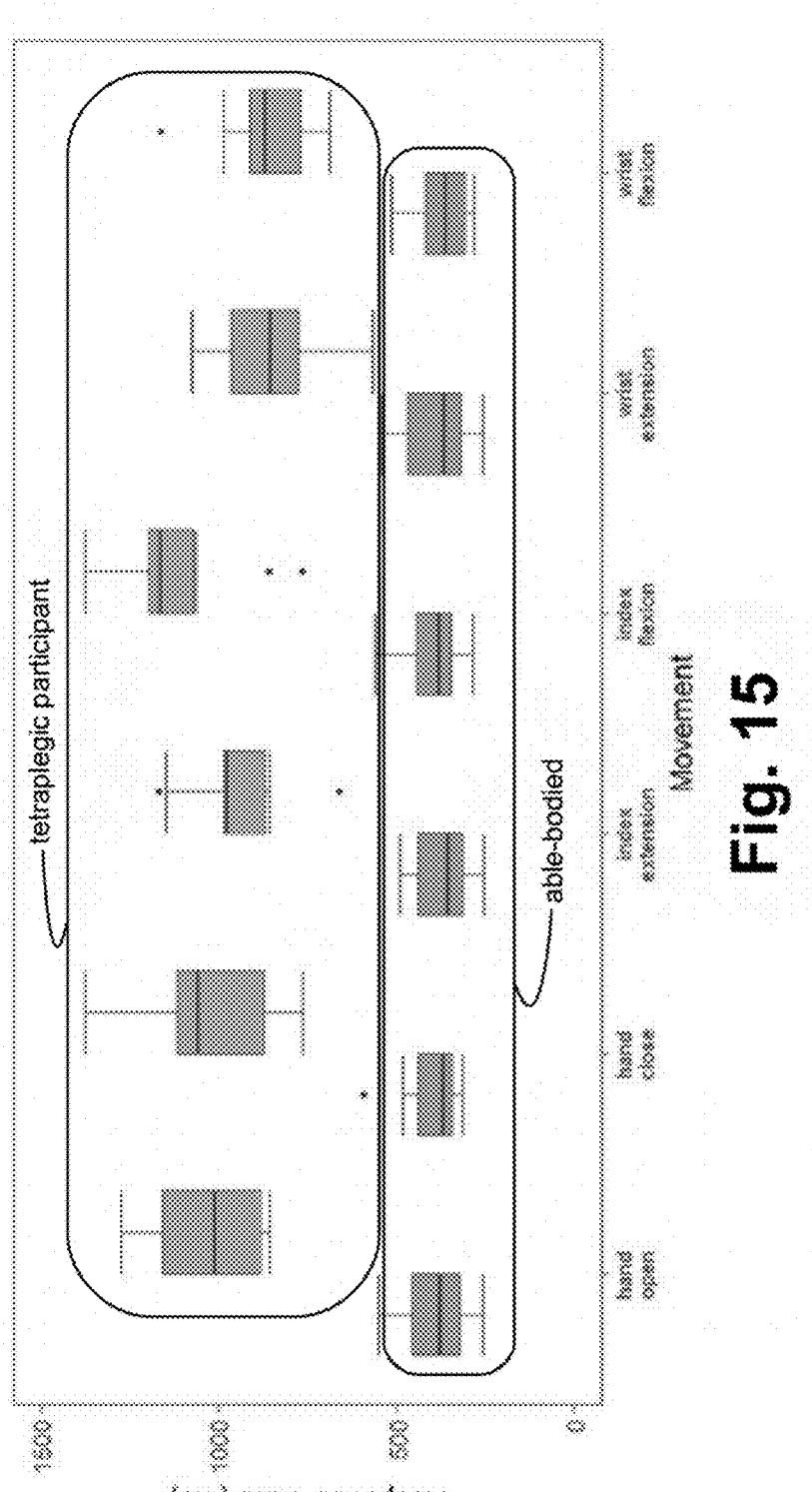

FIG. 15 presents response times of able-bodied individuals compared to the tetraplegic (i.e. SCI) participant response times measured from videos. This is a boxplot of the response time for the six-movement task broken out by each of the hand movements.

FIG. 16 presents a table of response times for each participant by hand movement (mean±s.d.).

Figure 17:
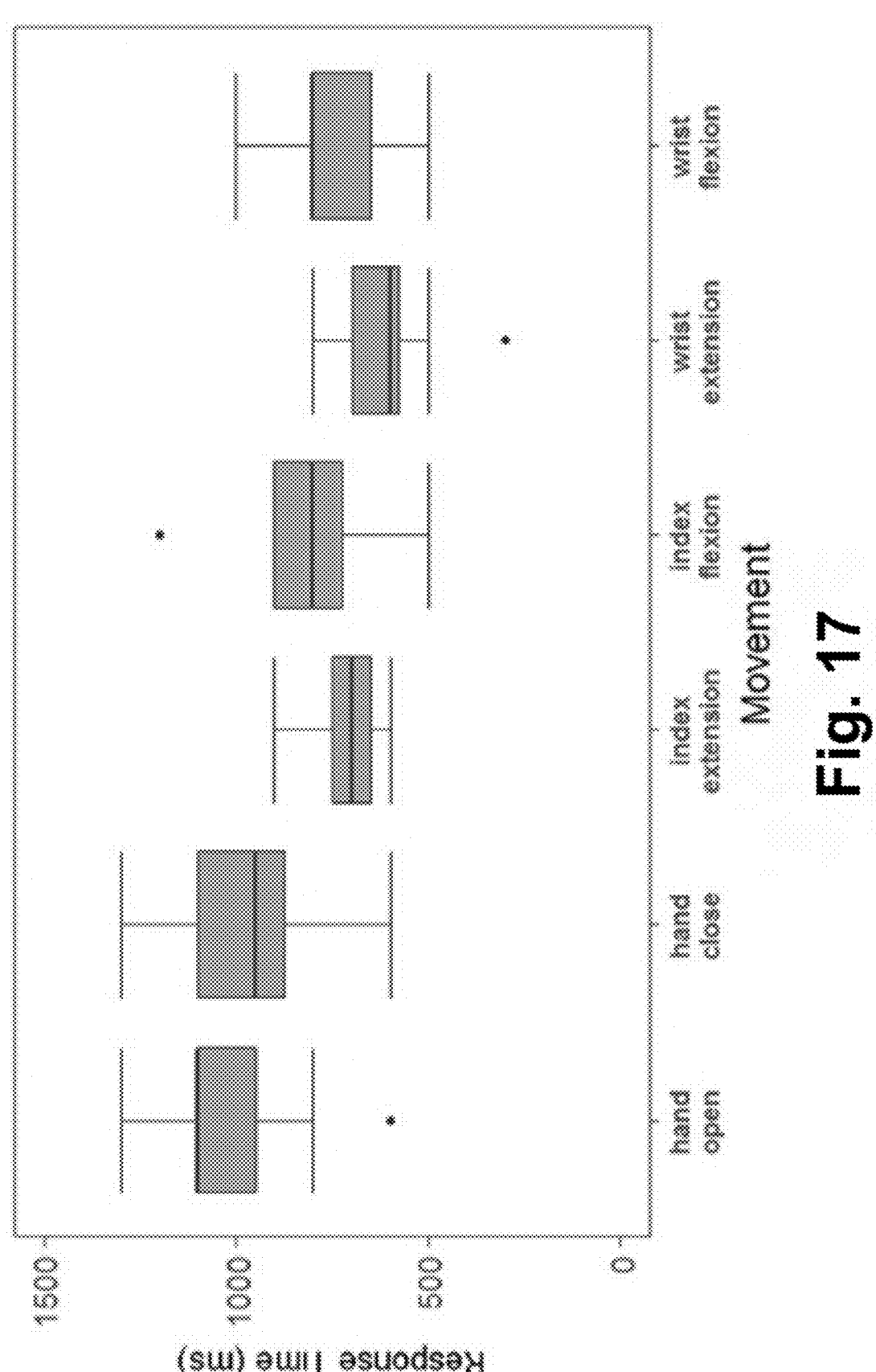

FIG. 17 presents response times of the tetraplegic (i.e. SCI) participant as measured by the decoder output. The decoder output was used to determine response times in order to separate the time that can be attributed to the algorithm versus the rest of the system. The response times based upon the decoder are about 200 ms less than the response times determined by the video, attributing 200 ms delay to the FES system.

DETAILED DESCRIPTION

The neural decoder component of the BCI—the algorithm that translates neural activity into control signals for assistive devices—is a key factor for various desired BCI characteristics. The decoder is responsible for inferring the user's intended action from a set of possible functions using the underlying neural activity. Thus, the decoding algorithm is directly tied not only to the number of functions/actions that can be decoded, but also to how accurately and how fast they can be decoded. Several studies have shown that, in addition to being identified as a priority of potential BCI users, the response time—the time between the user intending to act and the BCI identifying the user's intention—impacts the BCI user's sense of agency, or feeling of being in control of the BCI action.

Neural decoders are generally calibrated initially and updated periodically for each user and set of functions, which can require a considerable time commitment from the user. Calibration of the decoder typically requires the user to imagine performing several cued, or scripted, actions in a controlled sequence, so that the decoder can learn the mapping between patterns of neural activity and intended action from data where the intended action is explicitly known, a process known as supervised learning. The calibration process is complicated by the fact that neural activity is highly variable from day-to-day, disrupting the learned mapping and often leading to decoders being recalibrated frequently to prevent a decline in performance, adversely affecting BCI set-up time.

A decoder for a clinically viable BCI system should meet BCI-user performance expectations for accuracy, response time, daily set-up time, and number of functions. The accuracy is preferably high (e.g., on the order of 90% or higher), and target response time is preferably fast. Reducing system response time to below 750 ms may be important for providing the user with a sense of agency, and for maximizing BCI acceptance and adoption as clinical devices. While potential BCI users have indicated a willingness to invest their time to initially calibrate the system, frequent recalibration after the initial setup is undesirable. Thus, minimizing or eliminating daily recalibration is an important characteristic of a clinically viable BCI decoder. Clinically viable BCI decoders should also aim to provide the maximum number of functions possible while still otherwise meeting performance expectations. Building such a decoder is complicated by the fact that some of the design criteria represent competing demands. For example, increased accuracy often comes at the cost of increased decoder calibration/set-up time and increasing the number of functions can lead to decreased accuracy.

In the following, a novel neural decoding framework is disclosed that combines a deep learning neural network model with an unsupervised updating procedure and addresses the various user-desired decoder characteristics. In this context, 'unsupervised' refers to learning from neural data when the intended action is unknown and the model must infer the action prior to being updated. The disclosed update procedure requires no intervention from the user and can be performed using data collected during practical usage of the BCI, thereby avoiding the need for explicit recalibrations. The decoder was evaluated using more than two-years of intracortical data collected from a tetraplegic participant. The neural network model is was calibrated using one year's worth of historical data and the performance of the unsupervised updating was tested with the second year's data. The disclosed decoding method displays highly accurate performance, is able to sustain this performance for over a year without explicit daily recalibration, responds faster than a current state-of-the-art method that requires greater set-up time, and has the ability to increase the number of available functions from four to six with minimal additional calibration. It is further shown that the participant can use the decoder, which is calibrated offline using historical data where the participant imagined performing hand movements with no feedback, in real-time to control functional electrical stimulation of his paralyzed forearm allowing him to perform four distinct hand movements with high accuracy. Overall, the results presented here represent an important advancement towards the clinical translation of BCI systems, and highlight the usefulness of considering user performance expectations when designing and evaluating neural decoding strategies.

Figure 1:
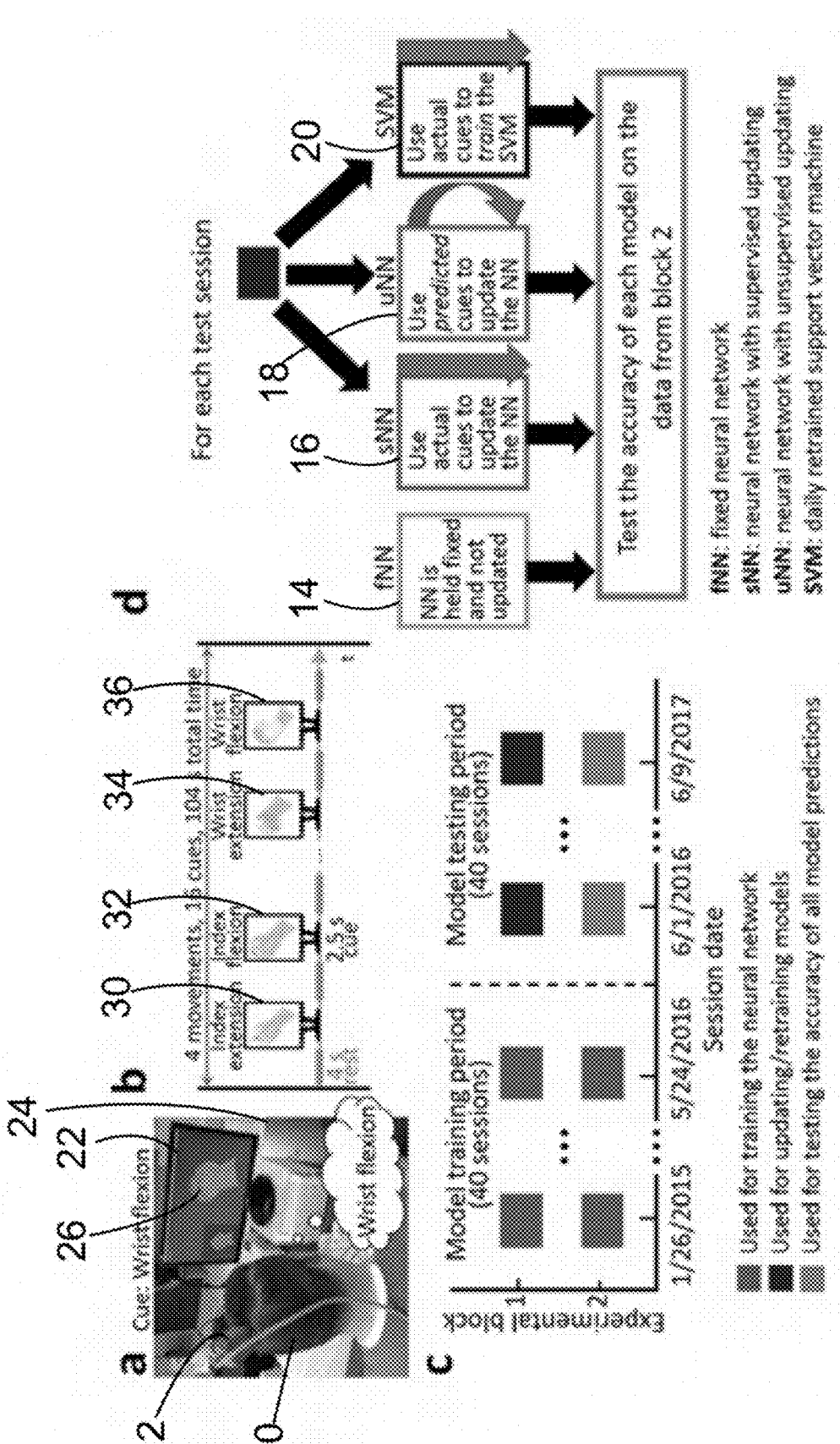
FIG. 1 diagrammatically illustrates a brain-computer interface (BCI) system as described herein.

With reference to FIG. 1, the study participant 10 is a 26-year-old male with a C5/C6-level complete spinal cord injury who was implanted with a 96-channel microelectrode array 12 in the hand/arm area of the left primary motor cortex. During a period of 865 days (80 sessions in total), the participant performed two blocks of the four-movement task, in which he was cued to repeatedly imagine executing four distinct hand movements in a random order, see FIGS. 1(a) and 1(b). Each block totaled 104 s. The data from these 80 sessions were then partitioned into training and testing periods for the neural network (NN) decoders (FIG. 1(c)). The training period data (40 sessions over the first year) were used to calibrate the fixed NN (fNN) decoder 14, which acts as the starting model for of all NN models. For each session during the testing period (40 sessions over the second year), the first block of data was used for updating two variants 16, 18 of the fNN 14, as well as calibrating a support vector machine (SVM) decoder 20 unique to that day (FIG. 1(d)). The two variants 16, 18 of the fNN 14 differed in how they were updated using the testing period data: either in a supervised manner (sNN) 16 or in an unsupervised manner (uNN) 18 (see FIG. 1(d)). The use of the SVM 20 as a baseline classifier was motivated by its success in a variety of classification problems as well as it's usage in several previous BCI studies. The performance of the decoding models 14, 16, 18, 20 was evaluated using the second block of data from each session during the testing period.

To reiterate, FIG. 1 diagrammatically depicts the participant 10 performing the four-movement task. As shown in FIG. 1(a), the movement is displayed on the computer screen 22 of a computer 24 by depiction of a virtual hand 26 on the display 22, and the participant imagines performing the movement. FIG. 1(b) shows the structure of one block of the four-movement task, which includes an index extension task 30, an index flexion task 32, a wrist extension task 34, and a wrist flexion task 36. Each of the four movements 30, 32, 34, 36 are repeated 4 times in a random order with 4 seconds of rest following each cue. FIG. 1(c) shows a layout of how the historical four-movement task data is used for the training and testing of the decoding methods. Each session consists of two blocks of the task, and the first 40 sessions (80 blocks) are used to train the neural network (see FIG. 2). The subsequent 40 sessions are the testing period, during which the first block can be used for updating/retraining a decoding model, while the second block is always used to test model accuracy. FIG. 1(d) illustrates how each of the four decoding methods 14, 16, 18, 20 use the data for a given test session. The fixed neural network (fNN) 14 is trained on the 80 blocks from the training period and not updated. The sNN 16 and uNN 18 both start as the fNN, but are updated using the data from the first block of a test session in either a supervised manner (for the sNN 16) or an unsupervised manner (for the uNN 18). The SVM decoder 20 is retrained every test session using only the data from the first block of that session.

Figure 2:
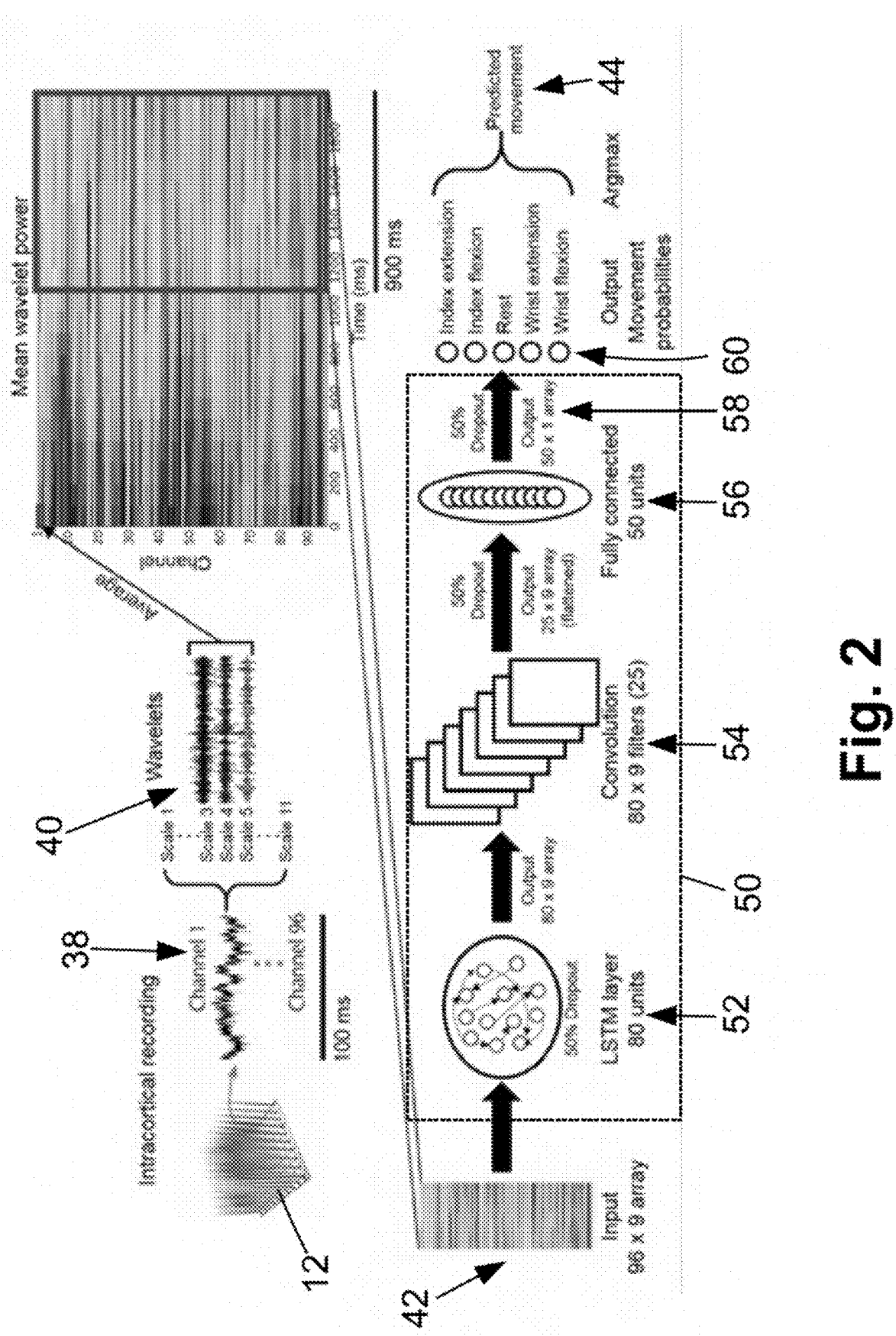
FIG. 2 diagrammatically illustrates the data processing and neural network model architecture of the BCI system of FIG. 1.

With reference to FIG. 2, neural features used by all models 14, 16, 18, 20 were mean wavelet power (MWP) values 40 calculated over 100 ms bins for each of the 96 channels of the 96-channel microelectrode array 12 and obtained through wavelet decomposition of raw voltage recordings 38 (see FIG. 2). MWP values for each of the 96 channels were lagged by 900 ms (9 bins), and the subsequent 96×9 array 42 was used as input to the NN models to generate a prediction 44 of the imagined movement at the current time point (FIG. 2).

More particularly, the raw voltage recordings 38 from each of the 96 channels were first processed in 100 ms segments. Wavelet decomposition was applied to the data, and the coefficients 40 from scales 3, 4, and 5 were averaged across time and then across scales in order to produce a single value, termed mean wavelet power (MWP), for each channel for each 100 ms time bin. The neural network then takes as input a sliding 900 ms window of the MWP for each of the 96 channels (forming the 96×9 array 42) in order to predict the intended movement for the current time point. The neural network 50 consists of a long short-term memory (LSTM) layer 52, a convolutional layer 54 with twenty-five 80×9 filters, a dense layer 56 with 50 units, and an output layer 58 that produces a vector 60 of 5 probability values (4 movements+rest). The movement with the highest probability value is the predicted movement 44 for that 100 ms time bin. It should be noted that each of the fNN 14, sNN 16, and uNN 18 is implemented using the NN model 50 as described with reference to FIG. 2, with the difference being whether and how the updating was performed: fixed (no updating) being the fNN 14; supervised updating for sNN 16, or unsupervised updating for uNN 18.

In contrast, the SVM 20 predicted the movement using only the current time bin's 96 MWP features as input.

With reference to FIGS. 3a and 3b, to investigate if the NN model 50 can decode intended movements with high accuracy, we first evaluated the performance of the sNN 16, in which the fNN model 14 was updated in a supervised manner utilizing explicit knowledge of the type and timing of movement cues during the first block of data from each session during the testing period. This daily update was done to control for any effects of time and focus solely on optimizing the accuracy component of decoder performance. FIG. 3a plots the accuracy (% of correctly classified time points in the second block) of the sNN 16 against the accuracy of the SVM 20 for each of the 40 sessions during the testing period. For comparison, the accuracy of the no-information decoder (the decoder that simply predicts rest since it is the most prevalent movement) is 61.54%. The bar plots of FIG. 3a show the marginal accuracy histograms for each of the two decoders. The plots show that the sNN 16 is more accurate than the SVM 20 for all sessions. In addition, for 37 out of 40 sessions, accuracy of the sNN 16 is greater than 90%. In contrast, accuracy of the SVM 20 is above 90% for only 12 sessions. To quantify the gain in accuracy displayed by the sNN, FIG. 3b compares the paired differences in accuracy between the sNN 16 and the SVM 20 for each session. Accuracy of the sNN 16 is significantly greater than the accuracy of the SVM 20 with a mean difference of 6.35±2.47% (mean±s.d., p=3.69e–8, V=820 using a paired two-sided Wilcoxon signed rank test).

With reference to FIG. 3c, it was next investigated whether the fNN model 14 could achieve and maintain high accuracy performance without the daily updating utilized by the sNN 16. This is motivated by users' stated preference for minimal daily setup time. We evaluated performance of the fNN model 14, which was calibrated using data from the initial 40 session training period (and never updated). FIG. 3c shows the accuracy of the fNN 14 (circular dots) plotted as a function of the number of days since the model was calibrated (i.e., the end of the training period). The accuracy of the SVM 20 is also included in FIG. 3c for reference (plotted triangles), but note that the SVM 20 is calibrated de novo every session during the testing period. The fNN accuracy is greater than the SVM accuracy for 36 out of the 40 sessions during the testing period. In addition, the fNN accuracy is above 90% for 32 sessions. The inset of FIG. 3c shows a box plot of model accuracies over the 40 testing sessions, showing that accuracy of fNN 14 is significantly higher than that of the SVM 20 (p=1.90e–7, V=798), with a mean difference of 4.56.±3.06%. Thus, the fNN 14 is able to sustain high accuracy decoding performance for over a year (381 days) without being recalibrated.

Interestingly, all models had their worst performance on post-training period days 238 and 266. According to the participant's medical records, these dates corresponded to times when the participant was in pre-treatment for undiagnosed infections. This observation reinforces the notion that many factors, including changes in the users' state of health, can influence the fidelity of decoding algorithms. Situations such as these reflect scenarios that clinical devices will encounter when placed in real-world settings, and it is desirable that BCI decoders do not simply break down after sessions with drastic drops in decoder performance. FIG. 3c shows that the fNN recovers from such encounters, performing at 94.24% accuracy on the last session of the testing period, 381 days after it was calibrated.

With reference to FIG. 3d, performance of the uNN 18 was investigated. Although the fNN 14 displays superior performance to the SVM 20, its accuracy is still lower than the sNN 16 which utilizes daily supervised updating (dots in FIG. 3d). Thus, we sought to improve the fNN 14 by leveraging data generated as the participant uses the system, but where the explicit intended movement is unknown a priori. Specifically, as data passes through the NN 50, the predicted movement from the NN model 50 can be used to provide tentative labels for the data, creating additional training data that can be combined with the previous data and used to update the model. In contrast to the sNN 16 where explicit knowledge of the type and timing of the movement cues is required for updating, in the case of the uNN 18, the model is first tasked with inferring these aspects of the movement from the neural data. This approach leverages all of the tentatively labelled data in the updating procedure and weights the influence of the tentatively labeled data proportional to the confidence in the predicted label. As this procedure does not require the collection of explicit calibration data or any other intervention from the user, it is referred to herein as the NN with unsupervised updating (uNN) 18.

To evaluate the uNN 18, we started with the fNN model 14 and updated it using the 40 sessions of training data plus the first block of data from each test session up to and including the one being evaluated. We did not use the intended movements from the first block in the update. The goal was to emulate data collected during practical usage where the user's intended movement will be unknown. FIG. 3(d) shows the accuracy of the uNN 18 (square symbols) during each session's second block as a function of the number of days since the end of the training period. FIG. 3(d) reveals that our unsupervised updating procedure increases the NN model accuracy over that of the fNN 14 and moves it closer to that of the sNN 16. The inset of FIG. 3(d) plots the difference in accuracy between the uNN 18 and the fNN 14, showing that the performance benefits of unsupervised updating increased over time. The mean gain in accuracy of the uNN 18 over the fNN 14 across the entire testing period was 1.56±1.36%, which is statistically significant (p=9.76e–8, V=807). Additionally, the uNN 18 provided a mean improvement in accuracy of 6.12±2.68% over the SVM 20.

Figure 3:
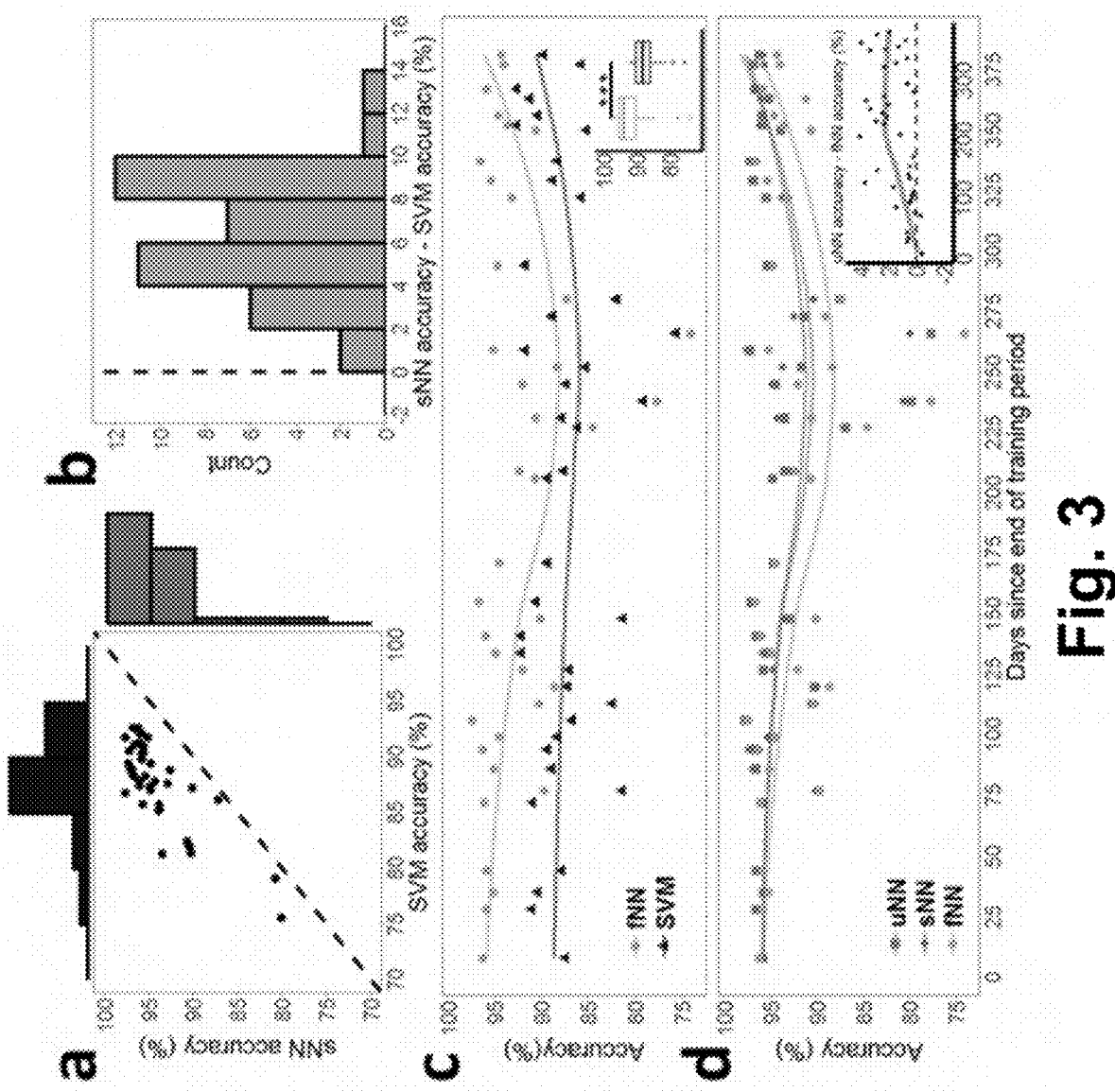
FIG. 3 presents experimental results for year-long high-fidelity decoding of movement intentions with neural networks performed with the BCI system of FIG. 1.

To reiterate, FIG. 3 shows year-long high-fidelity decoding of movement intentions with neural networks. FIG. 3(a) shows sNN accuracy for each of the 40 test sessions is plotted as a function of the corresponding SVM accuracy. Marginal histograms of the model accuracies are shown in the upper and right-most portions of the plot. FIG. 3(b) shows a histogram of the paired differences in accuracy (sNN-SVM) for each of the test sessions. The vertical dashed line denotes zero difference in accuracy. FIG. 3(c) shows fNN (circle symbols) and SVM accuracies (triangle symbols) plotted as a function of the number of days since the end of the neural network training period. The lines denote a LOESS smoothing curve to visualize the data trends. The inset of FIG. 3(c) shows a boxplot of the accuracies of the two models, where the stars denote that the difference in accuracy is significant (p<0.001, paired Wilcoxon signed rank test n=40, V=798). Note that the fNN model is held fixed and not updated while the SVM is retrained every test session. FIG. 3(*d*) shows the accuracies of the neural networks with either supervised (sNN, diamond symbols) or unsupervised (uNN, square symbols) updating are plotted along with the fNN accuracy (circle symbols). The inset of FIG. 3(*d*) plots the paired differences in accuracy (uNN-fNN) for each session during the test period.

The results of FIG. 3 compared decoding algorithms solely in terms of the accuracy in predicting the participants' imagined movement every 100 ms. Although accuracy is of importance to potential BCI users, it is difficult a priori to translate a 6.12% increase in accuracy to a tangible improvement in usability. Therefore, we explored additional usability criteria expected to be impacted by the choice of decoder. One such criterion is the response time, or the time it takes for the user to achieve the correct response from the system. We defined response times using the output of the decoder, requiring that the correct movement be maintained for at least 1 second. This provided us with an additional performance metric which we refer to as the failure rate: the percentage of cues where the model failed to predict and sustain the correct movement for at least 1 second. Table 1 shows failure rates for the uNN 18 and SVM 20 during block 2 of the testing period, with performance broken out by forearm movement. Table 1 presents the failure rate, or the percentage of cues where the model fails to predict the correct movement and maintain it for at least one second. Each movement is repeated 160 times resulting in a total of 640 cues over all test sessions. The numbers in parenthesis in Table 1 indicate the cues missed by the model. Overall, the retrained SVM missed 27.03% of the total cues, while the uNN missed only 11.56%.

TABLE 1

| | Failure rate (missed cues) | | | | |
|---|---|---|---|---|---|
| Model | Index extension | Index flexion | Wrist extension | Wrist flexion | All |
| SVM | 29.38% (47) | 33.75% (54) | 21.88% (35) | 23.13% (37) | 27.03% (173) |
| uNN | 11.25% (18) | 9.38% (15) | 13.75% (22) | 11.88% (19) | 11.56% (74) |

Figure 4:
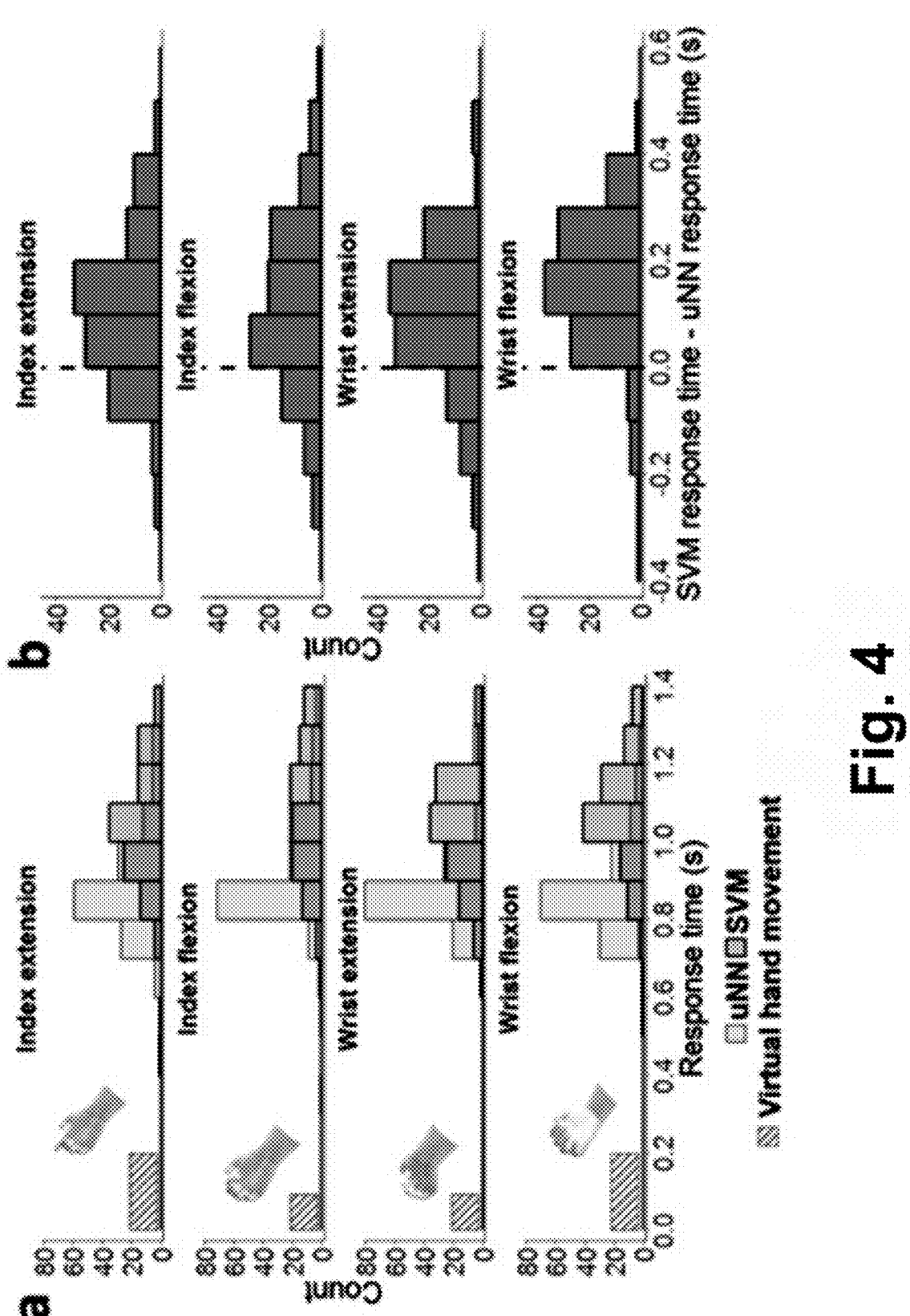
FIG. 4 presents experimental results for decoder responsiveness.

With reference to FIG. 4(*a*), we measured response time as the delay between cue onset and correct, continuous decoder activation for at least 1 second. We chose to measure response time from cue onset since the actual movement cues (i.e., the animations of a hand making the intended movement) take a variable amount of time to complete, as indicated by the hashed bars in FIG. 4(*a*). Thus, our estimates are most likely an overestimation as the participant recognizes the cued movement at some undetermined point during the animation. FIG. 4(*a*) shows a histogram of the model response times (uNN 18 in lighter shading and SVM 20 in darker shading) for each of the four movements. Because the decoder is updated in 0.1 s segments, response times were constrained to be multiples of 0.1. The response time of the uNN model (median 0.9 s) was faster than the SVM (median 1.1 s) across all movements (see Table 2, which shows median response times of the two models for each of the four movements). Again, these response times are measured right from cue onset. In the extreme case where it took the participant the full timing of the virtual hand movement to recognize the cue, the median model response times would then range from 0.7-0.8 s for the uNN and 0.9-1.0 s for the SVM (i.e., subtracting the movement animation durations from the response time). Thus, it is likely that the true model response times lie somewhere within these two cases, namely 0.7-0.9 s for the uNN and 0.9-1.1 s for the SVM.

TABLE 2

| | Median response time (s) | | | |
|---|---|---|---|---|
| Model | Index extension | Index flexion | Wrist extension | Wrist flexion |
| SVM | 1.1 | 1.1 | 1.1 | 1.1 |
| uNN | 0.9 | 0.9 | 0.9 | 0.9 |

With reference to FIG. 4(*b*), we next compared the paired differences in response time between the two models in cases where both models predicted the correct cue and maintained it for at least 1 second. FIG. 4(*b*) shows the histograms of these differences for all four movements. The uNN 18 responded significantly faster than the SVM 20 for all movements (all p<1e-10; index extension: n=112, V=4138.5; index flexion: n=104, V=3683.5; wrist extension: n=120, V=5313; wrist flexion: n=123, V=6702.5), with a median improvement of 0.2 s.

In summary, FIG. 4 shows that the neural network with unsupervised updating (uNN 18) responds more quickly than the daily retrained SVM 20. FIG. 4(*a*) shows histograms of the time it takes for the model to begin predicting the correct movement the user is imagining and maintain that movement for at least 1 second. The left insets of FIG. 4(*a*) show in shading the time it takes from cue onset for the virtual hand to complete the cued movement, e.g. 0.2 s for both index extension and wrist flexion and 0.1 s for both index flexion and wrist extension. FIG. 4(*b*) shows histograms of the paired differences in response times (SVM-uNN) for those movements where both models responded correctly. The dashed vertical line in FIG. 4(*b*) denotes zero difference in response time. The 6.12% increase in accuracy of the uNN 18 relative to the SVM 20 translates into a potentially clinically significant 200 ms improvement in response time and 15.47% improvement in failure rate (99 fewer misses).

The following experiments demonstrate real-time control of functional electrical stimulation (FES) using the uNN 18.

Figure 5:
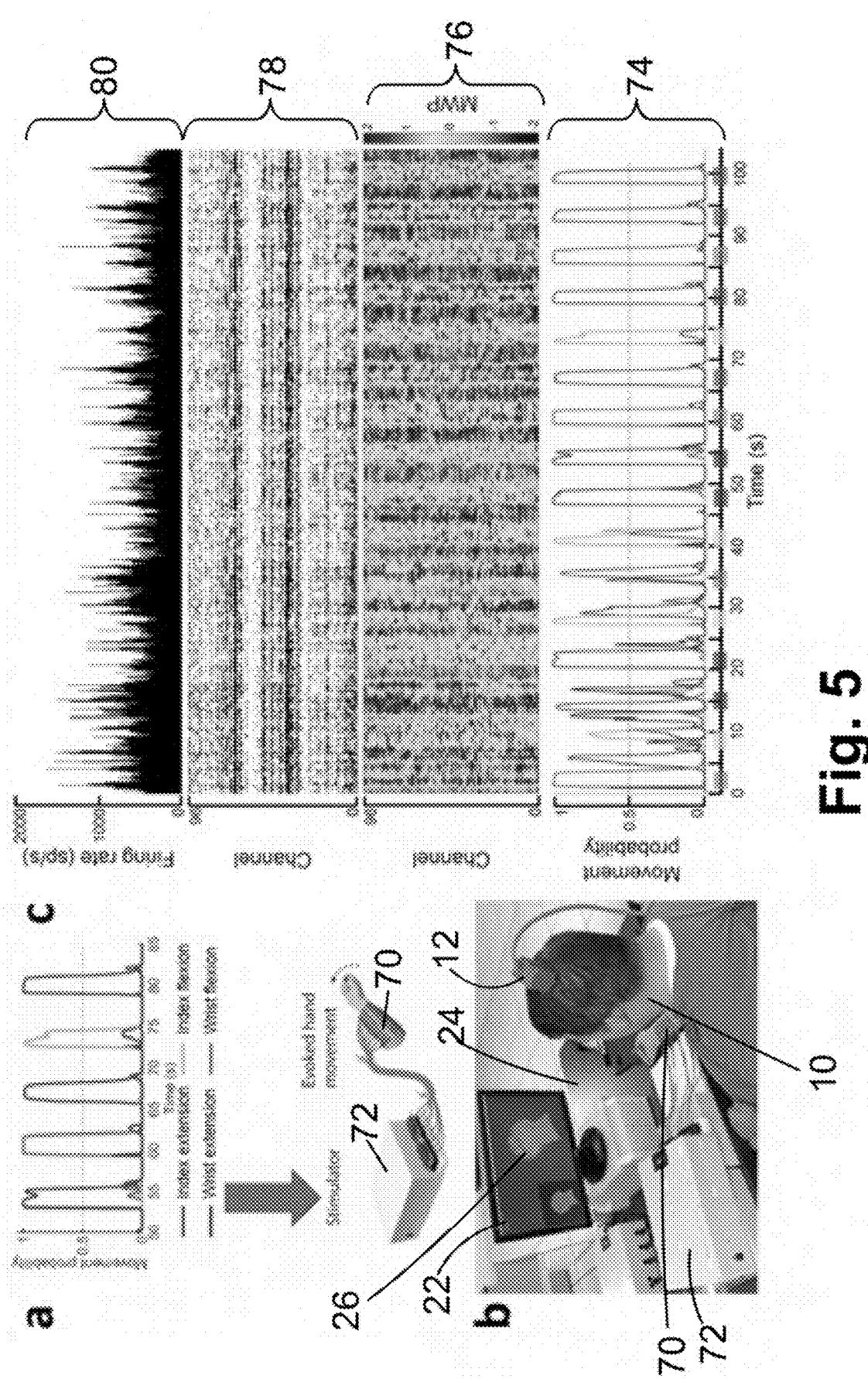
FIG. 5 diagrammatically illustrates the BCI system of FIG. 1 employed to control a functional electrical stimulation (FES) system.

With reference to FIG. 5, and initially referring to FIG. 5(*b*), to investigate whether the uNN model 18, which was trained and previously tested on imagined movements from historical data, would work in real-time for online BCI control, we designed an experiment where the participant 10 was required to use the uNN-BCI decoder implemented via the computer 24 to control a functional electrical stimulation (FES) device 70 worn on his paralyzed forearm to enable movements. The FES device 70 used a flexible cuff with 130 electrodes to stimulate forearm muscles and evoke cued movements every 100 ms based on decoder outputs. The FES device 70 was driven by an FES stimulator 72 connected with the computer 24.

In overview, FIG. 5(*a*) shows the output of the neural network decoder (i.e., the movement with highest predicted probability, corresponding to output 44 of FIG. 2) which was used to control functional electrical stimulation (FES) of the participants' paralyzed forearm. The participant 10 wore the flexible cuff FES device 70 consisting of 130 electrodes as shown in FIG. 5(*b*). Patterns of stimulation corresponding to the four movements (index extension, index flexion, wrist extension, and wrist flexion) were determined offline. The uNN decoder 18 was updated in an unsupervised manner using a single block of the four-movement task where the participant 10 received scripted stimulation (via the depiction of the virtual hand 26 on the display 22), and then was used in subsequent blocks to allow the participant to control the FES system 70, 72. FIG. 5(*c*) shows an example block where the participant was in control of the FES system 70, 72. FIG. 5(*c*) shows the output of the neural network decoder (bottom plot 74) along with the MWP features (plot 76) and spike times 78 for each of the 96 channels. The cued movement times are shown as the solid color blocks at the bottom of FIG. 5(*c*) (cues are shifted by 800 ms to account for reaction and system lag times). The top plot 80 shows the overall all firing rate across the 96 channels. Spiking features are shown only for visualization purposes as the decoder was built on MWP features.

The FES experiment consisted of three blocks. The first block utilized scripted stimulation of the four cued movements and was used for further unsupervised updating of the uNN 18. After this update, the uNN 18 was then held fixed for the subsequent blocks. In the next two blocks, the participant 10 controlled the FES device 70 using the uNN model 18. As in the standard four-movement task, the participant 10 was cued to perform repetitions of the movements in a random order. The participant 10 was able to successfully perform the movements in both blocks with accuracies of 85.06% and 84.77%, respectively, and individual movement accuracies shown in Table 3. Specifically, Table 3 shows individual movement accuracies for the two blocks where the participant was in control of the BCI-FES system. FIG. 5*c* shows data from the second block, including the output of the uNN decoder 74, MWP data 76, and threshold crossing data 78 (provided for reference only). The participant 10 appeared to have some difficulties early in the block with a few false positive movements occurring during the first 5 cues. However, he quickly recovered, and was highly accurate on the remaining 11 cues.

The participant's accuracy on the two blocks where he was in control of the BCI-FES system is lower than uNN model accuracy for purely imagined tasks. This is to be expected as electrical stimulation and both visual and movement feedback contribute additional variability to the neural data and the model was exposed to only a single unsupervised block of data with FES. We expect that real-time accuracy would improve significantly with further use, as it would provide additional experiential data with electrical stimulation and feedback for updating and\or training the model. This demonstration reveals that the uNN decoder 18 can be both quickly adapted to a condition that differs significantly from training conditions, and also used in real-time to control FES to the participant's paralyzed forearm.

TABLE 3

| | | Individual accuracy | | |
| --- | --- | --- | --- | --- |
| Block | Index extension | Index flexion | Wrist extension | Wrist flexion |
| 1 | 95.70% | 97.75% | 95.61% | 91.89% |
| 2 | 94.43% | 96.58% | 97.66% | 94.24% |

The next experiments investigated increasing the number of available functions with minimal training. Potential BCI users would like to maximize the number of functions the BCI can provide. However, end-users also want to minimize setup and training time, presumably even when adding new functions. Thus, it would be beneficial if the system allowed for the addition of new movements with minimal retraining. Therefore, we investigated whether transfer learning could extend the neural network to include additional functions with minimal training. In transfer learning, the learned parameters of a neural network model initially trained on one task are repurposed, or transferred, to a new, but similar, task. By leveraging the parameters learned for the initial task, the transfer model can be calibrated using substantially less data than the initial model. The implication for a NN-based BCI system is the potential to increase the number of movements available while requiring significantly less calibration time to learn the new movements.

Figure 6:
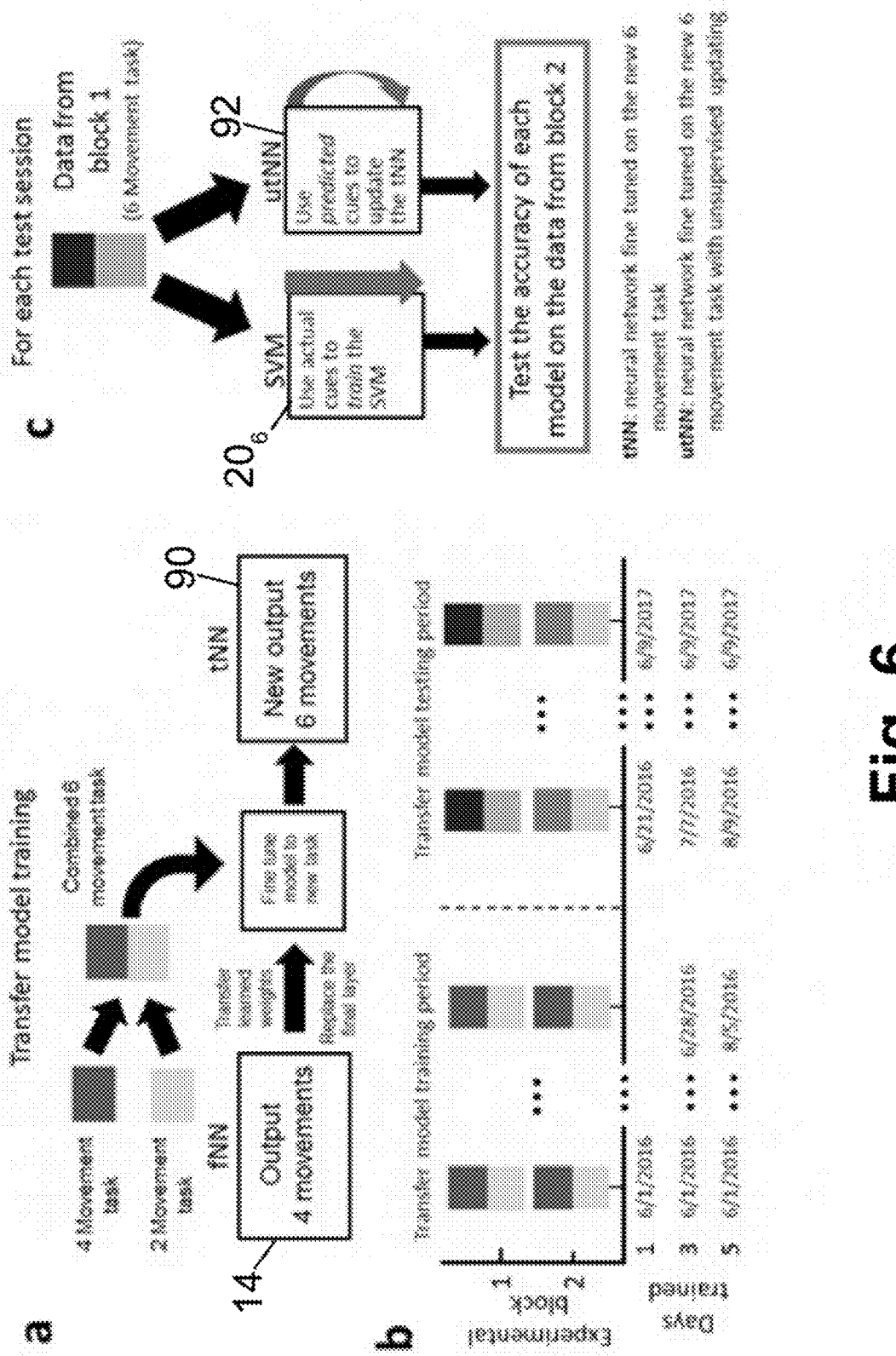
FIG. 6 diagrammatically illustrates updating the BCI system of FIG. 1 to increase the number of available movements using transfer learning and additional historical data.

With reference to FIG. 6, the learned features from the original fNN decoder 14 calibrated for four-movements were first transferred to a new decoder 90 with seven functions—the previously used four movements, rest, and two new movements: hand open and hand close. FIG. 6(*a*) shows an overview of the transfer model training, in which the transfer-learned neural network is referred to herein as the transferred NN (tNN) 90. Data from the four-movement and two-movement tasks from the same day are concatenated to create the training data for the tNN 90. FIG. 6(*b*) shows the layout of how the historical six-movement task data is used for the training and testing of the tNN 90. Each session consists of two blocks of the combined six-movement task, and the first 1, 3, or 5 sessions following the initial training period for the fNN 14 (see FIG. 1) are used to train three separate versions of the tNN 90. The subsequent 39, 37, or 35 sessions are the transfer model testing period, during which the first block can be used for updating/retraining a decoding model, while the second block is always used to test how accurately a model predicts the cue (or intended movement) given only the neural data. FIG. 6(*c*) shows how each of the two decoding methods use the data for a given test session. As with the uNN 18 (see FIG. 1), the tNN models 90 are updated in an unsupervised manner using the first block of data from each session during the transfer model testing period. We refer to this model as the unsupervised update tNN (utNN) 92.

To evaluate how much additional data was required to adequately calibrate, we trained three separate versions of the model using 1, 3, and 5 sessions of supervised data from the transfer model training period (FIG. 6(*b*)). After the initial training, the same unsupervised updating process as the uNN model 18 was employed during the transfer model testing period, resulting in a set of models we refer to as transferred NN models with unsupervised updating (utNN 92, see FIG. 6(*c*)). The utNN models 92 were compared to an SVM decoder 206 that was recalibrated to all six movements plus rest each day during the transfer model testing period.

Figure 7:
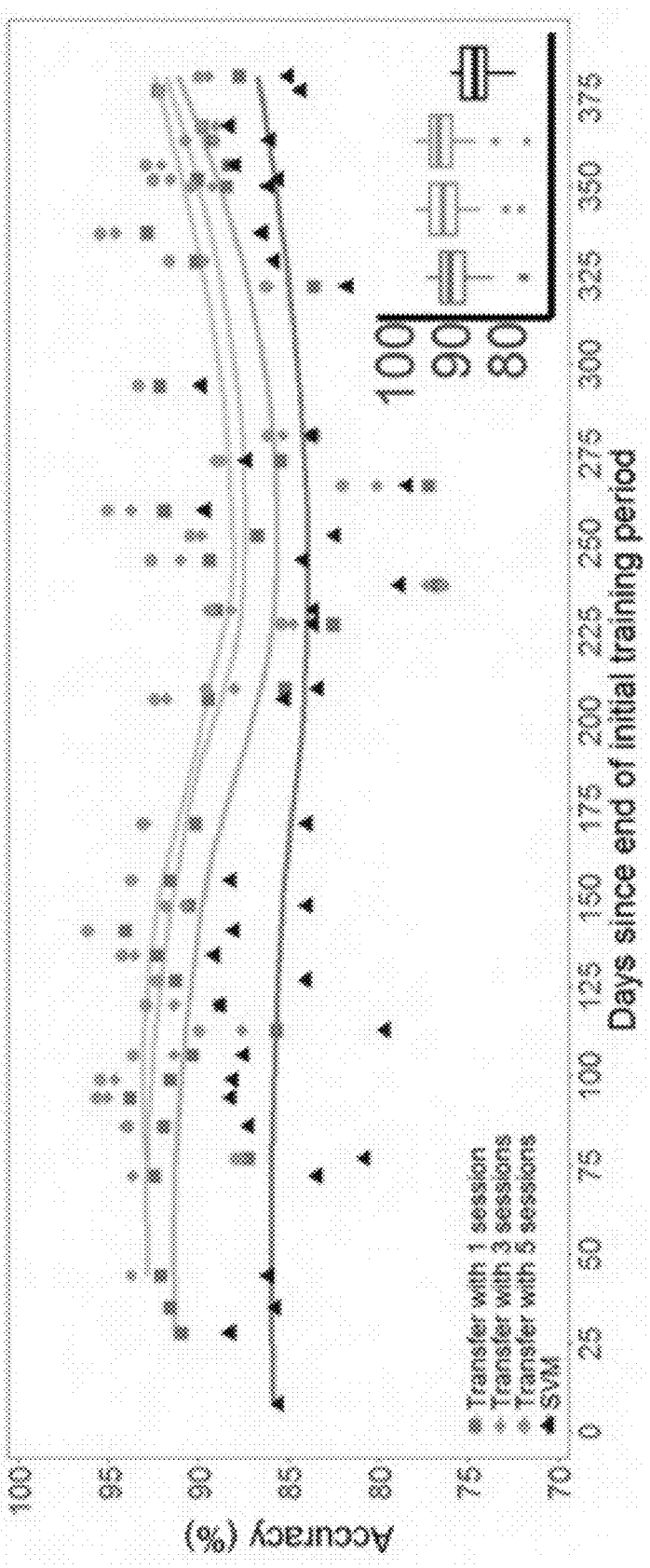
FIG. 7 presents experimental results for the transferred neural network model of FIG. 6 for decoding six movements after training using transfer learning.

With reference to FIG. 7, it is seen that the transferred neural network model can accurately decode six movements after being trained on a minimal amount of data. The transferred NN models with unsupervised updating (utNN) 92 consistently demonstrated superior accuracy to the retrained SVM 206 during the transfer model testing period. The accuracy of the utNN models 92 trained using either 1, 3, or 5 sessions' worth of data (square, diamond, and circle symbols, respectively) and SVM (triangle symbols) are plotted in FIG. 7 as a function of the number of days since the end of the initial neural network training period. The lines denote a LOESS smoothing curve to aid in visualizing the data trends. The three utNN models 92 vary in the number of sessions of six-movement data used in the initial training, and as expected, the more data used the higher the accuracy. The inset of FIG. 7 shows a boxplot of the accuracies of the four models (shown in the inset in order from left to right: utNN with 1 session transfer; utNN with 3 sessions transfer; utNN with 5 sessions transfer; and retrained SVM), in which the transfer with five sessions of data is, on average, higher than the other models and the SVM is, on average, the lowest performing mode.

To reiterate, FIG. 7 plots the accuracy of the utNN 92 and SVM 206 decoders as a function of the number of days since the end of the initial fNN training period. Using a single day of training for the new movements in the transfer model yielded an average accuracy of 88.89±4.18% (n=39), while increasing the amount of training data to three and five sessions resulted in average accuracies of 90.37±4.32% (n=37) and 90.97±4.27% (n=35), respectively. In comparison, the SVM had an average accuracy of 85.44±4.14% (n=40). Interestingly, the utNN with only a single session of additional training data, which amounts to 6.7 minutes of new calibration data, performs significantly better than the SVM (3.34±2.70% difference in accuracy on average, p=1.01e−7, V=601, n=39) during the testing period.

The results are further discussed below.

Four priorities indicated by the potential users of a BCI system include accuracy, set-up time/sustainable performance, response time, and the number of available functions. These priorities are all primarily affected by the neural decoder component of the BCI system. Disclosed herein is a neural decoding framework that directly addresses potential BCI user performance expectations. The disclosed decoder displays highly accurate (>90%) performance, sustains this performance for over a year without requiring user intervention or recalibration, responds faster than a current state-of-the-art method that requires greater set-up time, and can learn additional functions from only a few examples. We demonstrated these results using more than two-years of intracortical data collected from our participant with tetraplegia. In addition, we showed that our decoder, which is calibrated using historical data where the participant imagines performing hand movements with no feedback, can be used in real-time to control functional electrical stimulation of the participants' paralyzed forearm, allowing him to accurately perform four distinct hand movements.

A major barrier to creating accurate and robust neural decoders for BCI systems is the high degree of variability in neural activity both within and across recording days. This variability, which is caused by a variety of factors including electrode degradation and the user's cognitive state, violates the assumptions of standard statistical decoding models which assume the mapping between neural activity and intended action remains consistent over time. Thus, decoders that do not account for this variability generally incur a steady decline in decoder performance over time. The most common approach to combat this decline is to recalibrate the decoder prior to every use. However, this requires the users to undergo daily calibration tasks, leading to an undesirable increase in system set-up time. To avoid daily recalibration, one set of approaches are aimed at using data collected during practical use in order to continuously adapt the parameters of the decoder to changing recording conditions. While studies using these methods have been able to show sustained performance for at most a year, they typically utilize linear decoding methods, which can be less accurate than more complex nonlinear methods. More recently, Sussillo et al., "Making brain-machine interfaces robust to future neural variability", Nat. Commun. 7, (2016), have demonstrated in primates that a specialized recurrent neural network decoder for computer cursor control calibrated on a large amount of historical data (up to 50 sessions consisting of ~500 trials) can greatly outperform a simpler daily recalibrated decoder and sustain this superior performance for up to 59 days without recalibration. However, as the decoder relies solely on historical data to learn a static mapping between neural activity and intended action, from their plots, the decoder does appear to begin to decline in performance over time, albeit at a slow pace.

The methodology disclosed herein combines aspects of these two approaches to combat decoder performance decline. We use a flexible neural network model decoder that was initially calibrated on a year's worth of historical data (40 sessions totaling 2.31 hours) for four hand movements. Next, we showed that the parameters of the model could be updated in an unsupervised manner using data collected during practical system use. Importantly, this update procedure requires no intervention from the user, and can be performed during times of low system usage, for example, overnight while the user is asleep or during other periods of user inactivity. This innovative approach, combining a flexible neural decoder with unsupervised updating, led to uNN-BCI performance that averaged 93.78±4.39% accuracy when decoding hand movement over 40 sessions spanning 381 days. The boost in performance due to the unsupervised updating is evident in the inset of FIG. 3*d*, where the uNN steadily improved over the fNN as the initial calibration data aged. Additionally, the uNN failed to predict and sustain the correct cue only 11.56% of the time. In contrast, a daily-recalibrated SVM decoder had an average testing period accuracy of 87.66±3.85% and missed 27.03% of the total cues. Thus, the uNN not only meets 90% accuracy but also simultaneously eliminated daily decoder set-up time during the testing period.

In addition to accuracy and sustainable performance, potential BCI users also have cited response time as a design priority. Psychophysical experiments with BCI users indicate that response time should be minimized, ideally under 750 ms, as sense of agency—the feeling of being in control of the BCI system, which is an important factor in user acceptance—decreased as response time increased. While our median response times from movement cue onset of both the uNN 18 and the SVM 20 (900 ms and 1100 ms, respectively), fell outside of 750 ms, it likely that these times are overestimations as the participant was cued by on-screen animations with variable durations. Regardless, the uNN 18 still responds faster and is able to do so without being recalibrated prior to every use.

Potential BCI users also prioritize the number of available functions in the design of BCI systems. Decoders based on neural networks may be superior to other implementations because of their ability to easily use transfer learning to add new functions after the initial decoder calibration. We show that this secondary update to add more movements requires a minimal amount of additional data, is more accurate than a daily-retrained SVM decoder, and sustains the superior performance to the SVM over an extended period with the use of our unsupervised updating procedure. Thus, our framework provides the potential for BCI systems to be designed in a manner that allows for the quick addition of new functions to meet user demands.

We also demonstrated that the uNN trained on imagined movements could be used in real time to control electrical stimulation of the participants' paralyzed forearm. This demonstrates that the insights gained from the offline data can carry over to an online BCI scenario. That is, the features learned by the uNN after being calibrated using purely imagined data where the user receives no feedback can be transferred to the very different situation where the user is in control of FES and receiving visual and movement feedback. Generalization from patterns learned through offline training to online function required only a single block of data, consisting of 4 repetitions per movement, where the participant received scripted stimulation and the model was updated in an unsupervised manner. It is also worth noting that although here the uNN was used to control FES for hand movement, a similar strategy can be applied to control a robotic arm, computer cursors, and communication or other assistive devices.

Requiring 40 training sessions spanning 484 days to calibrate the BCI decoder would likely be undesirable to a potential user. However, the 40 sessions used here to calibrate the fNN amount to only 2.31 hours of actual training data. The practical usage data we use in our unsupervised updating procedure is collected in controlled conditions while the participant was being cued to imagine performing the movements. Although we do not use these cues when updating the model, the structured task he performed may have introduced differences compared to strictly passive data collection, as other confounds that can appear during practical use such as user distraction and frequency of actions may not be as comparable. Also, although we demonstrated that two new movements could be added with a minimum amount of additional calibration data, new movements cannot be added to the model ad infinitum. There is a finite amount of information contained in the array data that will enforce a practical ceiling on the performance as the number of movements increase.

Some additional details of the experiments are provided next.

The study participant was a man with tetraplegia from traumatic SCI suffered four years prior to his enrollment. A Utah microelectrode array (Blackrock Microsystems, Inc., Salt Lake, Utah) was implanted in the hand area of his left primary motor cortex on Apr. 22, 2014. During the previously described experiments, the participant viewed a computer monitor where two animated hands were displayed (FIG. 1a). Cues to think about specific movements were given by a small hand in the lower left corner of the screen. A larger hand centered on the screen provided real-time feedback from the BCI system during experiments where the participant had volitional control and was given visual feedback. Otherwise, the feedback hand remained in a neutral resting position.

The initial training dataset was based on a four-movement task in which the participant was cued to imagine either wrist flexion, wrist extension, index finger flexion, or index finger extension on each trial. Movement cues (2.5 s each) were shuffled and interleaved with rest cues (4 s each) as in FIG. 1b. One block consisted of four repetitions of each movement, for a total of 16 movements across 104 s. During each session, two consecutive blocks of data were collected with a brief rest period in between. In total, the participant performed this task 128 times from Jul. 18, 2014 (60 days after he first used the BCI system) to Jun. 9, 2017. Analyses in this paper were restricted to datasets collected between Jan. 26, 2015 and Jun. 9, 2017 in order to allow for participant recovery time from the surgery and adjustment to the overall BCI system set-up. This provided 80 sessions of data, representing 640 repetitions of each of the four movements across 16,640 s (~4.62 hours). The first 40 session "training period" spanned 484 days between Jan. 26, 2015 and May 24, 2016. The subsequent 40 session "testing period" spanned 373 days between Jun. 1, 2016 and Jun. 9, 2017 (FIG. 1c). The time from the last training day to the last testing day was 381 days.

The additional dataset used to train and test for transfer learning was based on a two-movement task in which the participant was cued to imagine opening or closing his hand on each trial. Movement cues (2.5 s each) were shuffled and interleaved with rest cues (6.5 s each). One block consisted of five repetitions of each movement, for a total of 10 movement cues across 98 s. Two blocks of data were collected at each session. In total, the participant performed this task 146 times from May 19, 2014 (the first day he used the BCI system) to Jun. 9, 2017. Analyses in this paper were restricted to datasets collected between Jun. 1, 2016 and Jun. 9, 2017.

In both experiments, the participant received no feedback, limiting his ability to adapt to specific decoders, and making these datasets well suited for testing different decoding algorithms.

Data was collected at 30 kHz from the Utah microelectrode array with 1.5 mm electrodes using the Neuroport™ neural data acquisition (Blackrock Microsystems). A 0.3 Hz first order high-pass and a 7.5 kHz third order low-pass Butterworth analog hardware filters were applied to the data. The data were then transferred to a PC running Matlab R2014b and Python 2.7 for further processing.

The 30 kHz data were reduced using a wavelet decomposition with a 'db4' mother wavelet and 11 wavelet scales. Features for decoding were created by extracting the wavelet coefficients for scales 3, 4 and 5, spanning a frequency band from 234-1,875 Hz. Every 100 ms, the coefficients were averaged over time, providing $96*3=288$ features for each 100 ms time bin. Next, these averaged wavelet coefficients for each channel were individually standardized by subtracting out the mean and dividing by the standard deviation of each feature over a single block of data. During the training period, each block of data was standardized to itself, while during the testing period, the mean and standard deviation of the first block was used to standardize both the first and second blocks. Once the 288 features were standardized, the 3 averaged and standardized coefficients for each channel were then averaged together to create a single feature, called Mean Wavelet Power (MWP), for each channel, resulting in 96 features for each 100 ms time bin. Lastly, the MWP features for each channel were smoothed by replacing the current time point with the average of the most recent 10 time points (i.e., a 1 s boxcar filter). To account for reaction and system lag times, the timing of the cues was shifted by 800 ms when training and calculating model accuracy. The cues were left un-shifted when calculating the model failure rates and response times.

The fNN 14 was constructed and trained with Python 2.7 using the package Keras with TensorFlow™ as the backend. The model architecture is shown in FIG. 2. It takes as input a 96×9-dimensional array 42 corresponding to 900 ms of MWP data. That is, the model uses a sliding window of 900 ms to predict the imagined movement for the current time point. The first layer in the network is the long short-term memory (LSTM) layer 52 containing 80 hidden units. The LSTM is a variant of a recurrent neural network which is widely used in the processing of temporal (or sequential) data. The hidden units in the LSTM layer use the hard-sigmoid activation function while the output of the layer uses a hyperbolic tangent activation. The LSTM layer outputs an 80×9-dimensional array that is passed to the one-dimensional convolutional layer 54 that contains twenty-five 80×9-dimensional filters. The convolution is performed in the time domain only. The activation function for the output of the convolution layer is a leaky-rectified linear unit with an a parameter of 0.01. The output of this layer is then flattened to a 225-dimensional vector which is then passed to the fully connected (dense) layer 56 with 50 units using the rectified linear unit activation function. The output from this layer is passed to a final dense layer 58 containing 5 units corresponding to the 4 movements plus rest. The units in this final layer use the softmax activation function scaling the outputs to correspond to probabilities. The unit with highest probability is the predicted movement 60 for that particular time-point.

The fNN 14 was trained using random batches of size 800 using the optimizer RMSprop and the categorical cross-entropy loss function. All network parameters were randomly initialized at the start of the training using the Keras defaults. During each training epoch, each layer in the model underwent a random 50% dropout of the connections weights in order to prevent overfitting to the training data (see FIG. 2). The training lasted for 100 epochs and took a total of 493.55 seconds to complete using an NVIDIA Quadro K5000 GPU on a Linux system running Centos 7.3. The two other NN models, the sNN 16 and uNN 18, both begin life as the fNN 14 but differ in how they utilize data from the testing period for additional refinement.

The separate support vector machine (SVM) classifier 20 nonlinear Gaussian radial basis functions kernels with a γ parameter value of 0.005, was trained using the MWP features extracted from the first block of data for a given session, and uses the MWP features at the current time point only in order to predict the intended movement. The SVM was trained using the sci-kit learn toolbox in Python 2.7.

Supervised updating of the NN model (that is, sNN 16) occurred as follows: On the first session of the testing period, the MWP features and cues were extracted from the first block of data. This data was combined with the training period data to create a larger training dataset for the model. Next, the weights of the NN model were initialized to the fNN 14 described in the previous section. This new model was then updated by running the same fitting procedure on the new training dataset for 30 epochs. The performance of this model was assessed using the second block of data. This process was repeated for each session during the testing period, with new data added to the updated training dataset every session, and the same fitting procedure applied to models initialized with weights from the previous session. The supervised aspect of this procedure refers to the fact that the actual cues used in the experiment were used in updating the model.

The unsupervised updating procedure for uNN 18 differed from the supervised procedure in the manner in which labels of cues were obtained. In the supervised case, the known experimental cues were used to label the MWP data from the first block. In the unsupervised case, the current model was first used to predict the cues for the first block of data for each session. The MWP data and the predicted cues were then combined with the training period data as described above. In addition, the fitting procedure was slightly different for the two types of updating: in the unsupervised case, the loss function was changed to the "hard" boot strapping modification of the cross-entropy function. Briefly, this loss function allowed for the explicit inclusion of "noisy" labels by modifying the regression target in the cross-entropy function to include a convex combination of the noisy label and the model's currently predicted label. Next, as in the previous paragraph, the fitting procedure with the new loss function was run for 30 epochs to update the model, and the process was repeated for each session during the testing period. Thus, the unsupervised aspect of this procedure refers to the fact that the labels for the data used in the updating were generated by the model itself and did not require the user to participate in a cued recalibration task.

Transfer learning and fine-tuning are methods of taking information from previously trained NN models and applying it to a new or refined task. To create the dataset for this demonstration, experimental blocks collected on the same day from the four-movement and two-movement tasks were concatenated and treated as a new six-movement task (FIG. 6a).

Next, we initialized the transferred NN (tNN) 90, a new NN model with analogous structure to the fNN 14 except for the output layer, which had 7 units instead of the previous 5. The tNN was initialized using weights from all layers except the output layer from the fNN 14; weights for the tNN's output layer were initialized randomly. In the first stage of training, all the weights were held fixed, except the output layer weights which were calibrated using the cross-entropy loss function with a batch size of 400 and run for 30 epochs. This repurposing of the output layer of a neural network model is referred to as transfer learning. Once transfer learning was complete, we performed additional fine-tuning of the tNN: Weights for all the entire model were updated for an additional 20 epochs, resulting in a fully trained model (tNN 90) for the combined six-movement task.

Three separate versions of the utNN 92 were trained by using both blocks of data of the combined six-movement task from either 1, 3 or 5 sessions (6.7 minutes, 20.2 minutes, or 33.7 minutes of total data respectively). During the transfer model testing period, the models were updated using the unsupervised procedure previously described, combining the six-movement training data with the predictions on the first block of the testing period (FIG. 6c). Each of the updated models was tested on the second block of data for the given session. For each subsequent session in the testing period, the predictions on the first block were added to the training set for the remainder of the testing period.

Performance measures used were as follows. Accuracy refers to the percentage of the total number of 100 ms time bins in a given block where the decoding model correctly predicted the cued movement. Accuracy of individual movements were computed as the one-versus-all (one movement against all other plus rest) accuracy for each movement. A locally weighted polynomial regression (LOESS) curve with smoothing parameter equal to 0.9 were added to accuracy plots to help better visualize the trend. The model response times were estimated by finding the first time point after cue onset where the correct movement was predicted and sustained for at least 10 consecutive time bins (1 second).

Real-time control of functional electrical stimulation experiment was done as follows. In this experiment, the uNN model decoder 92 controlled functional electrical stimulation (FES) of the participants' paralyzed forearm. The FES system 70, 72 consists of the multi-channel stimulator 72 and the FES device 70 comprising a flexible cuff consisting of up to 130 electrodes that is wrapped around the participant's arm. See FIG. 5(b). Offline, electrode stimulation patterns corresponding to the four movements in this task were calibrated using knowledge of forearm physiology and trial and error. The uNN decoder 92 was used to predict the participant's intended movement every 100 ms and the predictions were used to select the appropriate stimulation pattern, which was then actuated by the FES system 70, 72 to carry out the desired movement (FIG. 5A). The stimulation pulse rate was 50 Hz and the pulse width was 500 µs. Artifacts induced by the electrical stimulation were detected in the raw data by using threshold crossings of 500 µV occurring simultaneously on at least 4 of 12 randomly selected channels. A 3.5 ms window of data around each detected artifact was then removed and adjacent data segments were rejoined. This approach removed most of the artifact while leaving a minimum of 82.5% of the original data.

The dataset included three blocks of data collected on Aug. 4, 2017. The first block was analogous to the four-movement task except the participant also received scripted stimulation corresponding to the cued movement. The uNN model 18 that had been updated up until Jun. 9, 2017 was used to predict the cues for the first block after it had been standardized. The MWP data for this block along with the predicted labels were used to update the model for a total of 5 epochs using "hard" boot strapping modification of the cross entropy function. This is slightly different from the unsupervised updating we performed previously, as we did not add this block to the larger training set before performing the update. The reasoning behind this choice is because the neural data with the electrical stimulation was quite different from the historical data without the stimulation, and we wanted the model to adjust to the stimulation data without biasing the updating towards the imagined data (which makes up the vast majority of the training data). Next, the mean and standard deviation of the first scripted block were used to standardize the subsequent two blocks, in which the updated model was used to control FES feedback in real-time. The model was only updated in an unsupervised fashion using the scripted stimulation data from the first block, and the participant used the model to control the FES system for the next two blocks.

Two-tailed paired Wilcoxon signed rank tests were performed for all between model comparisons of accuracy and response times.

Further Comparisons

In the following, some further comparisons the deep neural network (DNN) model of FIG. 2 with the SVM model are described. It was found that response time increases and accuracy decreases as the number of functions increases for both decoders. However, we show that this slowing of response times and decline in accuracy with added hand functions is significantly less for the DNN than the SVM. Interestingly, we find that data preprocessing steps affect the response times of the two decoders in different ways. We further show that the DNN decoder can be used in real-time to control functional electrical stimulation (FES) of the participants' paralyzed forearm, allowing him to perform six different hand/finger movements. Also, to establish quantitative benchmark that can be used to evaluate the performance of the BCI-FES system against an ideal target we collected data from three able-bodied individuals who performed the same six-movement task. These results help characterize BCI decoder performance features relevant to potential users and the complex interactions between them.

These comparisons involved the same participant 10 described previously, with the experimental setups previously described with reference to FIG. 1 (for imagination experiments) or FIG. 5 (for FES control experiments). The computer monitor 22 displayed two animated hands to the participant (FIGS. 1(*a*) and 5(*a*)). For the imagined movement tasks (FIG. 1), the cues to think about specific movements were given by a small hand in the lower left corner of the screen 22. During rest periods, the hand remained in a neutral position. During experiments where the participant had volitional control of functional electrical stimulation (FIG. 5) and was given visual feedback, the larger hand centered on the screen provided real-time feedback from the BCI system. Otherwise, the feedback hand remained in a neutral resting position.

For offline analyses, data was collected from two separate tasks where the participant imagined making hand/finger movements without controlling FES or receiving visual feedback on performance. These imagined tasks allow for the independent evaluation of algorithms without the confounding effect of the participant adapting to the decoder that is generating the feedback. The two-movement task cued the participant to imagine hand open or hand close for 2.5 s separated by 6.5 s of rest (the rest cue showed the virtual hand in a neutral position). Each movement was replicated five times and the presentation of the cues was randomly shuffled to prevent the participant from anticipating the next cue. We called this entire 90 s (25 s of cues and 65 s of rest) sequence a block. The four-movement task cued the participant to imagine performing index extension, index flexion, wrist extension, and wrist flexion. Each movement cue lasted for 2.5 s and movement cues were separated by 4 s of rest. Each movement was repeated four times and, as with the two-movement task, the movement cues were randomly shuffled. Each block of the four-movement task lasts 104 s (40 s of cues and 64 s of rest). FIG. 1B shows an illustration of the structure for a typical block.

Two blocks of both the four- and two-movement experiments per session were collected during fifty experimental sessions ranging from Jun. 1, 2016 to Nov. 28, 2017. The first forty sessions were treated as training data and the remaining ten sessions were considered the testing data.

Figure 8:
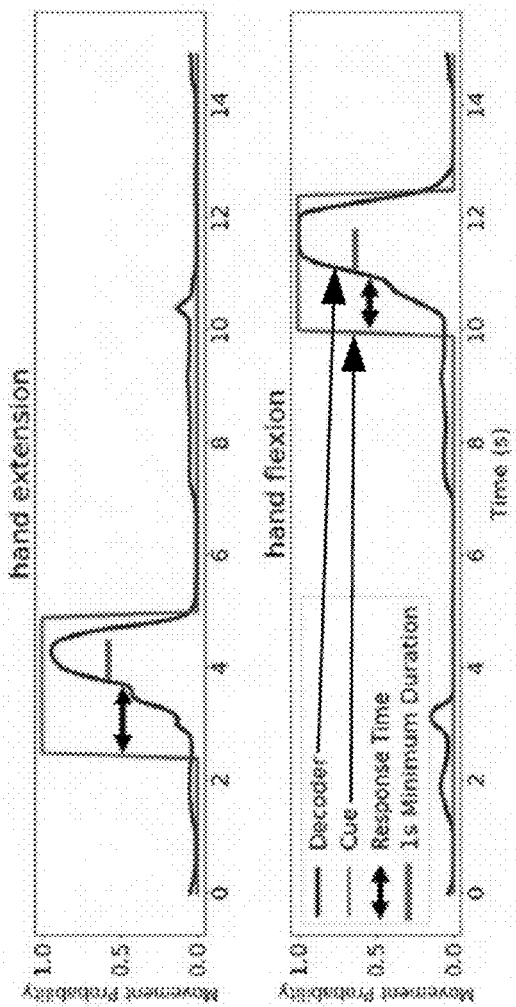
FIG. 8 presents a sample decoder output for the hand extension task (top plot) and the hand flexion task (bottom plot). demonstrating the response time. Response time is the difference between the start of the cue to when the decoder output initiates the correct movement. To be successful, the movement must be sustained for a minimum of 1 s.

With reference to FIG. 8, the result of a cued movement was considered to be successful if the correct movement was predicted and sustained for a minimum of 1 s within the 2.5 s cue time window. In FIG. 8, the cue time window is rectangular while the decoder signal is a curved trace. The success rate for an experimental block was defined as the percentage of cues in the block that were successes. The failure rate was the percentage of cues that are not successes. Ensuring that the correct response was sustained allowed us to filter out functionally irrelevant situations where the decoder correctly predicts the cue for a brief window and then switches to predicting a different, erroneous movement. To further quantify decoder performance, we also calculated the decoder accuracy, defined as the proportion of 100 ms time bins where the decoder correctly predicted the cued hand movement.

To demonstrate the different accuracy metrics consider the 90 s two movement task which has ten movement cues. The success rate is the percentage of the 10 cues where the correct movement was predicted continuously for at least 1 s. In contrast, the accuracy is the percentage of the 900 time bins (90 s$\times$10 time bin/s) where the decoder prediction matched the cue. The success rate is meant to approximate an observer scoring each movement cue as a success or failure, whereas the accuracy is the standard machine learning classification accuracy.

Response time was defined as the time between the start of the cue to the initiation of a successful movement (where success was defined as above). In offline analyses, the initiation of the successful movement was determined by the first 100 ms time bin where the decoder predicted the correct movement and sustained the correct prediction for at least 1 s (FIG. 8) In the real time demonstrations, where hand movements were evoked, the initiation of the correct hand movement was calculated from the first frame of video where the hand began moving toward the cued position for a successful movement. Note that for both the response time and success rate, the first cued movement was ignored because the DNN starts predicting during the middle of cue due to the time lagged input.

Data was collected at 30 kHz from the 96 channel Utah microelectrode array with 1.5 mm electrodes using the Neuroport™ neural data acquisition (Blackrock Microsystems). A 0.3 Hz first order high-pass and a 7.5 kHz third order low-pass Butterworth analog hardware filters were applied to the data. The data were then transferred to a PC running Matlab R2014b and Python 2.7 for further processing.

The raw data was reduced using wavelet decomposition with the "db4" mother wavelet and 11 wavelet scales in Matlab R2014b. Features for decoding were created by extracting the wavelet coefficients for scales 3, 4, and 5, spanning frequency range 234-1,875 Hz. Every 100 ms, the coefficients were averaged over time, providing 96*3=288 features per bin. Next, these averaged wavelet coefficients for each channel were individually standardized over a single block of data. During the training period, each block of data was standardized to itself, while during the testing period, the mean and standard deviation of the first block was used to standardize both the first and second blocks. Once the 288 features were standardized, the 3 averaged and standardized coefficients for each channel were then averaged together to create a single feature, called Mean Wavelet Power (MWP), resulting in 96 features, one per channel, for each 100 ms time bin.

Figure 9:
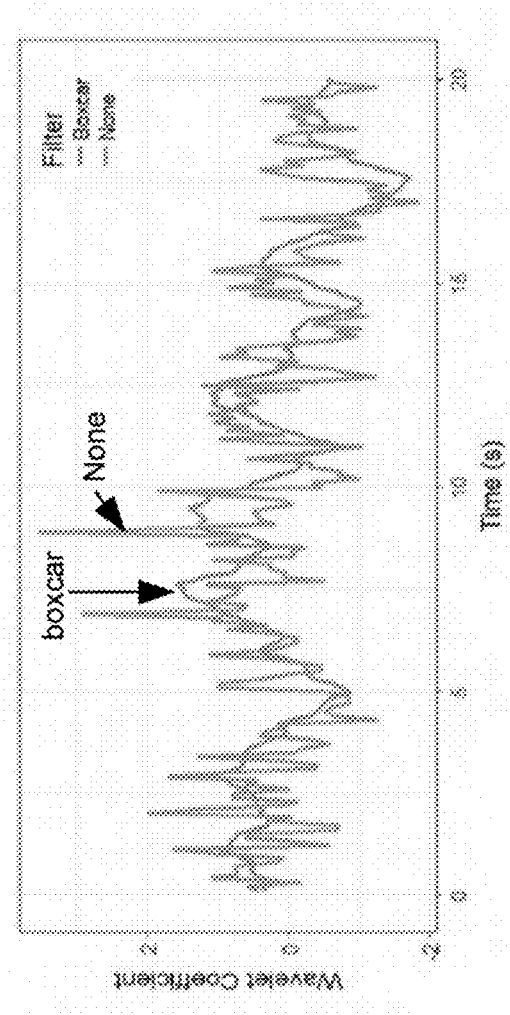
FIG. 9 presents impact of a boxcar filter on the wavelet coefficient across time for a single channel and wavelet scale.

With reference to FIG. 9, in these further comparisons, we performed an additional preprocessing step where the MWP features for each channel were smoothed by replacing the current time point with the average of the most recent 10 time points (i.e., a 1 s boxcar filter, see FIG. 9) on a subset of analyses to determine the effect of this preprocessing step on the two different decoders.

In these further comparisons, we evaluated two different decoding algorithms with respect to their impact on both accuracy and response time. The first decoding algorithm is the SVM classifier 20 described previously (e.g. FIG. 1). The SVM 20 is trained de novo each day during the testing period using only the first block of data and evaluated on the second block of data from the same day. That is, the SVM 20 is only ever trained on a single block of data, but it is retrained every single session. The SVM 20 uses nonlinear Gaussian radial basis functions kernels with a γ parameter value of 0.005 and uses the MWP features at the current time point only in order to predict the intended movement. The SVM was trained using the sci-kit learn toolbox in Python 2.7 using the default parameter values except for the value of the γ which we based on our previous experience using the SVM. The SVM retrained daily is used as the benchmark comparison since it reflects the standard of practice for this clinical study and daily retraining is the standard mode of operation for most intracortical BCI systems.

The second decoding algorithm is the deep neural network (DNN) decoder 50 (see FIG. 2) constructed and trained with Python 2.7 using the package Keras with TensorFlow™ as the backend. The DNN 50 takes as input the 96×9-dimensional array 42 corresponding to 900 ms of MWP data. That is, the model uses a sliding window of 900 ms to predict the imagined movement for the current time point. The first layer in the network is the long short-term memory (LSTM) layer 52 containing 80 hidden units. The LSTM 52 is a variant of a recurrent neural network that is capable of learning long-term dependencies and has been widely used in the processing of temporal (or sequential) data. The LSTM layer 52 outputs an 80×9-dimensional array that is passed to the one-dimensional convolutional layer 54 that contains twenty-five 80×9-dimensional filters. The convolution is performed in the time domain only. The output of this layer 54 is then flattened to a 225-dimensional vector which is then passed to the fully connected (dense) layer 56 with 50 units using the rectified linear unit activation function. The output from this layer 56 is passed to a final dense layer 58 containing units equaling the total number of movements plus rest. The units in this final layer 58 use the softmax activation function scaling the outputs 60 to correspond to probabilities.

The 80 blocks from the first 40 sessions of the two- and four-movement tasks were used to train the DNN model 50. The DNN was trained using random batches of size 200 using the optimizer RMSprop and the categorical cross-entropy loss function. All network parameters were randomly initialized at the start of the training using the Keras defaults. During each training epoch, each layer in the model underwent a random 50% dropout of the connection weights in order to prevent overfitting to the training data. The training lasted for 80 epochs and was completed using an NVIDIA Quadro K5000 GPU on a Linux system running Centos 7.3. The 80 epochs of training was based upon the model reaching a stable loss and accuracy value for the validation data during training. Subsequently, the number of training epochs was treated as a fixed hyperparameter (at 80) to prevent overfitting to the training dataset. The DNN's performance was then evaluated on the second blocks of each of the last 10 sessions.

To quantify the trade-off between accuracy, response-time, and the number of movements, the two- and four-movement datasets were concatenated in each session, creating an aggregate dataset with six separate movements. To create datasets that contained fewer movements, we excised data corresponding to different cues and created a series of synthetic datasets that covered the range of all possible combinations of the six hand movements (ranging from one to six movements). For example, there were six different one-movement datasets, one for each of the six movements, and one six-movement dataset. For each of the two through five-movement datasets, we created a synthetic dataset for every permutation of the different movements. In these synthetic datasets, data associated with cues for excluded movements were removed but all rest cues were retained.

A first experiment provided a real-time demonstration of the six-movement task. In this experiment, the DNN model decoder controlled functional electrical stimulation (FES) of the participants' paralyzed forearm. The FES system 70, 72 consists of a multi-channel stimulator 72 and a flexible sleeve 70 consisting of up to 150 electrodes that is wrapped around the participant's arm (see FIG. 5). Offline, electrode stimulation patterns corresponding to the six movements in this task were calibrated using knowledge of forearm physiology and trial and error. A six-movement task was performed using the same movements in the previous sections but with random rest intervals varying from 2 to 5 s and a cue time of 2.5 s. Each cue was repeated four times for a total of 24 movements per block. The DNN model 50 (FIG. 2) was first trained offline using the concatenated imagined six-movement dataset and was updated for 15 epochs using cued data from a single block. This model was then used for five blocks of the six-movement task within a single session on Jan. 15, 2017. The same DNN model 50 was then updated using the five blocks of collected data and trained for 10 epochs. This updated model was then used in a subsequent session to make predictions on the participants intended hand movements to direct the FES system 70, 72.

On Jan. 22, 2018 the participant performed three blocks of the six-movement task to assess his response times when using the BCI-FES system. The time from the start of the cue to the initiation of the hand movement was measured from using video data with a timer displayed on the monitor. Response time measurements were recorded as the time from cue presentation to initiation of the correct hand movement based upon the stopwatch in a video recording. Additional response times were computed for the tetraplegic participant 10 (see FIGS. 1 and 5) using the decoder outputs as previously described.

To establish a baseline for movement response times that could be used to quantitatively compare the response time of the BCI-FES system, three able-bodied participants (different individuals than the tetraplegic participant 10 previously described) also performed the six-movement task. The three able-bodied participants ranged in ages from 20 to 25 and volunteered to participate in the demonstration. The able-bodied participants were asked to perform the same six-movement task and were cued using the same animated hand and timing profiles described above. They were instructed to mimic the hand movements in a "natural and comfortable" manner. Each able-bodied participant performed 3 blocks of the six-movement task. Videos were recorded and the time from the start of the cue to the initiation of the hand movement was measured in the same manner as described for the clinical trial (i.e. tetraplegic) participant 10. The results were aggregated across the able-bodied participants and blocks to obtain average able-bodied response times for a given hand movement.

Figure 10:
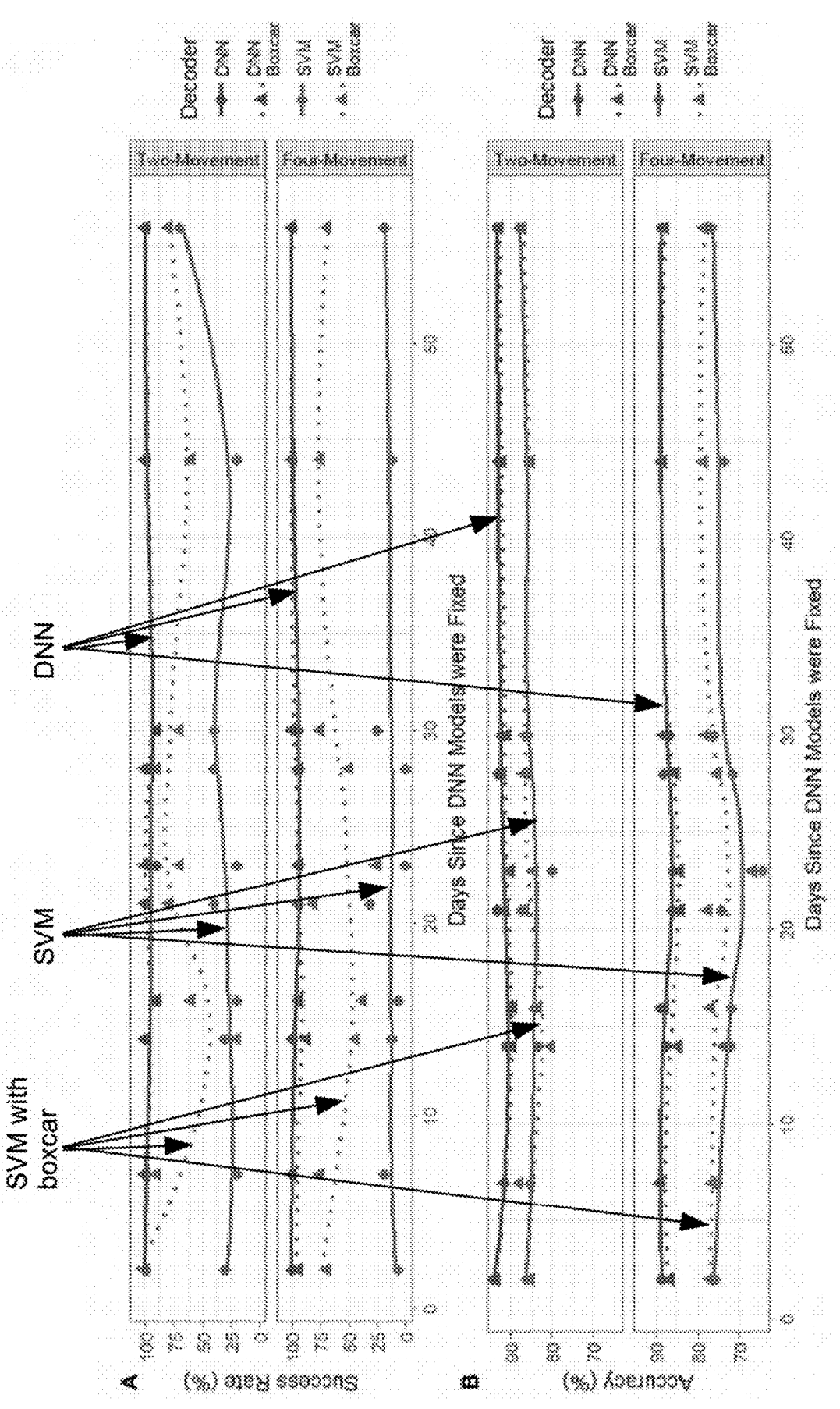
FIG. 10 part (a) presents success rate for both the two-movement and four-movement offline tasks during the testing period. Solid lines and circles are used to plot data for the boxcar filter and dashed lines with triangles are used to plot data without the filter.

With reference to FIG. 10, statistical analyses to compare the success rate or accuracy between paired observations were done with a Wilcoxon signed rank test. Comparisons across multiple groups were completed using generalized linear or ANOVA models. Analyses comparing regression slopes were conducted by the F-test for significance of slopes. In the following, comparisons of decoding and data preprocessing methods are described. We first explored the differences in success rates and response times for the two decoding methods on the two- and four movement tasks offline. FIG. 10(a) plots the success rate (% of cued movements where the model correctly predicts and sustains the correct movement for at least 1 s) of the decoders (SVM 20 and DNN 50) during the testing period as a function of the number of days since the end of the initial training period for the DNN. Recall that the DNN is trained on 40 sessions of historical data and then held fixed during the testing period while the SVM is retrained each day. Also shown is the success rate of the models when an additional preprocessing step (replacing the MWP at the current time point with the average of the most recent 10-time points, i.e., a 1 s sliding boxcar filter) is applied to the data prior to being input to the decoders. We have included this additional comparison (boxcar on vs. boxcar off) since we have previously found that including the boxcar filter is key to the SVM's decoding performance. This is illustrated in FIG. 10(a), which shows that the success rate of the SVM without the boxcar was significantly less than the SVM with the boxcar. The average success rate for the SVM on the four-movement (two-movement) task with the boxcar was 60.0±19.3 (71.1±23.0, mean±s.d.) while the success rate without the boxcar was 12.7±11.5 (28.9±17.5). In contrast, the success rate of the DNN appeared to be unaffected by the inclusion of the boxcar filter preprocessing step (compare solid and dashed lines). A two-way ANOVA of the success rate fit against the model type and the presence of the boxcar filter found that there were significant differences between both model type and use of the boxcar filter (p<0.001), except there was not a significant difference between the boxcar on and off DNN models. This finding was consistent for both the two- and four-movement tasks. The DNN's success rate without the boxcar (with the boxcar) was 97.3±3.4 (96.0±4.7) on the four-movement task and 96.7±5.4 (97.8±4.7) on the two-movement task. The classification accuracies (% of correctly predicted time bins) shown in FIG. 10(b) showed the same pattern. The DNN (SVM with boxcar) accuracy was 87.8±1.3 (75.9±3.6) on the four-movement task and 91.9±1.5 (85.2±2.2) on the two-movement task.

Figure 11:
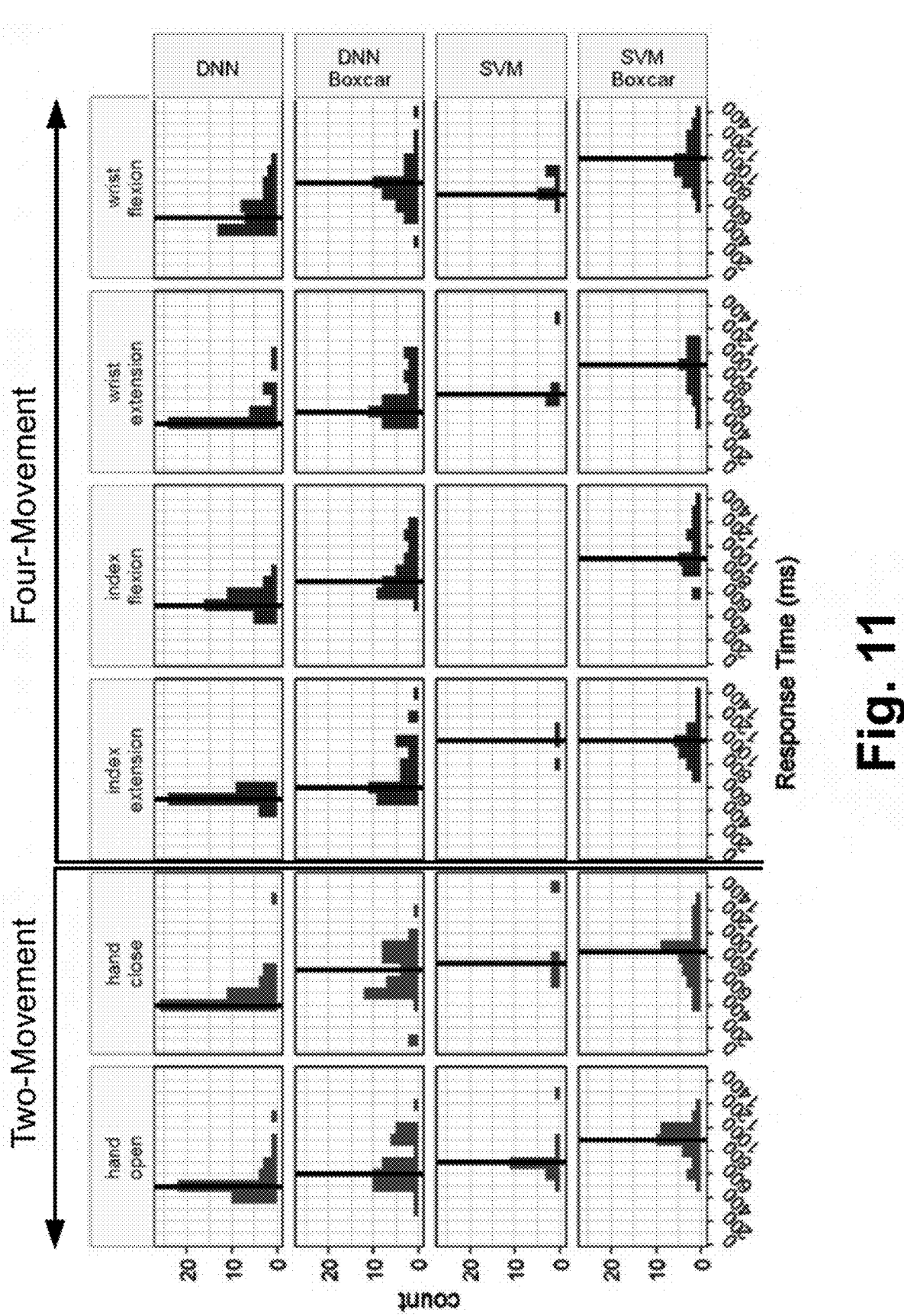
FIG. 11 presents histograms of response times for the offline tasks. The distribution response times for each successful hand movement across the testing period are shown, broken out by decoder-filter combination and task. Mean

With reference to FIG. 11, response times also significantly varied for each of the four models. Recall that the response time was calculated as the time from cue onset until the model predicts the correct cue and sustains it for at least 1 s. FIG. 11 plots histograms of the model responses times broken out by the individual movements from the two- and four-movement tasks. Even though the response times are aggregated by individual movement, note that the movements were performed in different tasks, i.e. two-movement tasks or four-movement tasks. The vertical line in each histogram indicates the mean of each distribution. Although we found the success rate for the DNN 50 was not significantly different whether or not the boxcar filter was used, there is a clear increase in response time when using the boxcar filter for both tasks (p<0.001). The mean response time for the DNN 50 across all movements on the four-movement (two-movement) task without the boxcar was 524±128 ms (506±150 ms), whereas the mean response time with the boxcar was 719±218 ms (683±211 ms). This makes intuitive sense as the boxcar filter averages past information in with the most current information (see FIG. 9), which smooths the data but can slow the model response times. As we have shown, this tradeoff allows for the SVM 20 to accurately decode the imagined movements, but is not required for the DNN 50.

The mean response time of the SVM with the boxcar filter on the four-movement (two-movement) task was 946±205 ms (855±196), which was significantly slower than both DNN models. Comparisons to the SVM without the boxcar filter were not conducted due to the poor success rate of the models (12.6 and 28.9% for the four-movement and two-movement tasks). These results show that the DNN model 50 does not require the additional preprocessing step of the boxcar filter and has both higher accuracy and faster response times than the SVM 20.

Performance trade-offs are next characterized via simulation.

Here, we conducted a simulation experiment which allowed us to use historical data from the two- and four-movement tasks to more fully quantify the performance characteristics as a function of the number of movements. The data sets from both tasks were concatenated for each experimental session yielding a synthetic six-movement task. We then excised data by movement from each set and created additional synthetic datasets ranging from each movement individually to all six movements. For the datasets that contained less than six movements, all possible permutations of movement combinations were extracted. For example, the one movement dataset consisted of each individual movement where data corresponding to all other movements were removed (i.e., one block of the six-movement task yielded 6 separate one-movement blocks). Next, for the two movement datasets, a dataset was created for each possible pair of movements. This was repeated for three, four five, and six movements leading to synthetic datasets for all possible permutations. Decoders were trained and tested for each movement combination and then aggregated according to the total number of movements. We chose to compare the SVM decoder 20 with the boxcar filter and the DNN decoder 50 without the boxcar filter as they were best performing combination for each algorithm as previously shown (see FIG. 10 and related discussion).

With reference to FIG. 12, plots are shown of the model accuracies for each test session as a function of the number of total movements. Note that even though there are only 10 test sessions, the number of data points shown in the figure can vary for the different numbers of movements owing to the fact that there are $$\binom{6}{k}$$

combinations for each total number of movements k. The data points in FIG. 12 are also randomly jittered in the x-coordinate for easier visualization. Overall, model accuracy during the testing set declined as the number of movements increased for both decoders. However, the rate of the decline was significantly greater (p<0.001) for the SVM (slope=−3.7, p<0.001) than the DNN (slope=−2.4, p<0.001), indicating a relatively greater cost to accuracy for additional movements with the SVM 20 compared to the DNN 50.

With reference to FIG. 13, we next explored how the individual movement response times changed as the number of total movements increased. FIG. 13 plots the average response time (averaged across testing sessions and movement combinations) as a function of the number of total movements, broken out by the specific movement and the decoding model. As expected, response time increased with the number of movements (DNN: slope=23.8, p<0.001; SVM: slope=11.82, p<0.001). The slope of the SVM does appear to be smaller than the slope of the DNN, but the difference was only marginally significant (p=0.046) based upon a likelihood ratio test comparing models with and without separate slopes for decoder. Although the timing varied by the movements themselves, the rates of change were not significantly different across the movements. The DNN 50 consistently had faster average response times than the SVM 20 across all movements. Additionally, the average response times across testing sessions, movement combinations, and individual movements ranged from 566±130 to 694±55 ms for the DNN and 862±130 to 914±63 ms for the SVM. For this task, increasing the number of total movements clearly leads to increased response times and decreased accuracy for both the DNN and SVM.

With reference to FIG. 14, we further investigated whether the models displayed a speed-accuracy trade-off in terms of their response times. FIG. 14 plots the average model response time as a function of accuracy for each test session broken out by model type and the number of total movements. The SVM 20 does not appear to have a significant interaction between accuracy and response time while the DNN 50 displays a negative interaction. That is, the faster responses correlate with more accurate responses, which makes intuitive sense since the accuracy is the percent of correctly classified time bins and decreasing the response time leads to increased chance of correctly classifying time bins within a cue time window. Thus, it appears that when decoding movement intentions from neural data, both accuracy and response time display a trade-off with the number of total functions, while accuracy and response time can either interact beneficially (DNN 50) or not significantly (SVM 20).

In the next set of experiments, performance of the tetraplegic participant 10 is compared with performance of the able-bodied individuals. Having found that the DNN displays the highest accuracy and shortest response times as the number of movements is increased, we tested how these performance gains might translate to a real time BCI control scenario. We designed an experiment where the tetraplegic participant 10 (who has spinal cord injury, SCI, hence also sometimes designated as the SCI participant) used the DNN decoder 50 to control functional electrical stimulation (FES) of his paralyzed forearm. The BCI-FES system (see FIG. 5) uses the flexible sleeve 70 with up to 150 electrodes to stimulate forearm muscles and evoke movements every 100 ms based on decoder outputs as previously discussed. When a movement is decoded, the predetermined FES pattern is triggered for that movement. The tetraplegic participant 10 used the BCI-FES system to perform three blocks of the six-movement task. Video recordings were used to determine the tetraplegic participants' response times for each of the cued movements. In addition to previous sections where response time was determined by the time from cue onset to the correct movement being decoded, here we also calculated the response time from cue onset to the time when the tetraplegic participant visibly initiated the correct movement with his own hand. This allowed us to quantify the time to actual movement and assess how much of that delay is due to the decoder. We also recorded three able-bodied participants performing three blocks of the same task to quantify ideal response times.

With reference to FIG. 15, a boxplot is shown comparing the response times of the tetraplegic participant 10 to those of the able-bodied participants. The able-bodied participants had an aggregate mean response time of 390±96 ms while the tetraplegic participant had a mean of 997±224 ms.

With reference to FIG. 16, a table is presented which shows the mean response times for each individual movement. Overall, these results indicate that the tetraplegic participant responds ~600 ms slower on average than the able-bodied participants.

With reference to FIG. 17, it is noted that the tetraplegic participant's response times in the experiment of FIGS. 15 and 16 are consistently higher than in the imagined movement experiments. When we computed the response times based on the decoder outputs as shown in FIG. 17, the response time of the decoder was 821±226 ms. In addition, there was on average a 176±311 ms delay between the decoder being active and the tetraplegic participant's hand beginning to move that can be attributed to processing time on both the computer and stimulator, the response of the tetraplegic participant's muscles to the stimulation as well as any variability in the video processing. The overall success rate of the tetraplegic participant was 76.4% whereas the able-bodied participants had a success rate of 100%.

In these further comparisons, we have explored the trade-offs that exist between accuracy, response time, and the total number of functions in decoders that infer discrete hand movement signals from intracortical neural recordings. Specifically, we trained and evaluated DNN and SVM decoders using historical data from the tetraplegic participant 10 where he imagined performing several different hand movements. Using synthetic datasets created from this historical data, we systematically investigated how increasing the number of decoded movements affects performance. Overall, we found that response time increases and accuracy decreases as the number of functions increases for both decoders, while accuracy and response time can either interact beneficially (DNN 50) or not significantly (SVM 20). We also performed an experiment where the tetraplegic participant used the DNN decoder 50 in real-time to control functional electrical stimulation (FES) of the tetraplegic participants' paralyzed forearm, allowing him to perform six different hand/finger movements. We then compared the tetraplegic participants' performance with the system to that of able-bodied individuals in order to quantify the response time delay induced by the BCI-FES system.

The manner in which the raw neural data is processed before entering the predictive model can have an impact on the performance of the model. With more sophisticated models, the impact of pre-processing may be more difficult to evaluate a priori. Our results show surprisingly divergent performance for two different decoding algorithms (SVM 20 and DNN 50) based on whether the input data was initially smoothed with a 1-s boxcar filter. We have used the boxcar filter to smooth the neural features prior to using them in the SVM 20. By averaging the neural data from the current time point with the previous nine time points we reduced the variance of the input features but lessen the effect of the most recent time point which may slow down the response time. However, as the SVM 20 only has access to the current time point and can thus make movement predictions based solely upon this single data point, including the boxcar filter effectively allows the SVM 20 to incorporate information from prior time points, thus improving prediction accuracy. This smoothing is useful for the SVM, as removing the boxcar filter decreases the success rate from 60.0 to 12.7%. However, the DNN 50 does not show this same reduction in performance when the boxcar filter is removed, as the success rate for the DNN 50 is not significantly different whether or not the boxcar filter is used. This can be attributed to the DNN model's ability to synthesize temporal patterns more effectively than the SVM. However, using the boxcar filter does increase the response time of the DNN 50 on average from 524 to 719 ms. Thus, data pre-processing can have a significant effect on decoder performance, but that effect can be highly dependent on the type of decoder used.

Furthermore, using synthetic datasets, we systematically changed the number of output functions from one to six and explored how these performance criteria interact with one another for the DNN and SVM decoders. We found that accuracy decreases as the total number of movements increases. We also found that response times tend to increase with the number of total movements. Interestingly, the performance detriment to accuracy and response times caused by increasing the number of movements was less severe for the DNN 50 than for the SVM 20, with the rate of decline in accuracy being significantly less with the DNN than SVM. Additionally, we found no interaction between response time and accuracy for the SVM 20 and a positive correlation between the two for the DNN 50. Though the positive correlation between response time and accuracy makes intuitive sense for BCI task presented here, it is counter to the trade-off observed for other BCI systems, such as those for virtual typing, where faster responses tend to be less accurate.

We further performed an experiment to quantify the gap in performance between the tetraplegic participant and able-bodied individuals. Assuming the ideal target response time for a potential (e.g. tetraplegic) BCI user would be the response time of an able-bodied individual, the difference between BCI and able-bodied responses provides a functional metric that can be used to gauge performance. Thus, we had the tetraplegic participant use the DNN decoder 50 in real time to control FES of his paralyzed forearm. We chose to use the DNN decoder 50 for this experiment as it performed better than the SVM 20 in our offline analyses. Using the BCI-FES system, the tetraplegic participant performed the six-movement task. As the decoders all had their slowest responses when six movements were enabled, having the tetraplegic participant perform this task in real-time provided a "worst-case" example to compare to able-bodied responses. Our results indicate that the tetraplegic participant responds about 607 ms slower on average than our able-bodied participants. The response time can be further subdivided into the time it takes for the decoder to accurately predict the user's intent (821 ms on average) and the lag between decoder activation and forearm movement (176 ms on average). This highlights that the neural decoder response latency is only part of the total response latency. While these results are necessarily dependent on the choice of decoding algorithm and the assistive device being controlled, quantifying the difference in latency of BCI responses from that of able-bodied individuals provides a useful benchmark that is broadly applicable and can be generalized to other systems that use intracortical activity.

In sum, we have characterized the performance trade-offs for the BCI-FES system using both SVM and DNN decoders across different combinations of pre-processing methods and number of functions. We found that the DNN 50 has several advantages over the SVM 20 including reduced data pre-processing requirements and less performance degradation with additional movements. We further showed that a subject with tetraplegia was able to use the DNN model 50 to control FES of his paralyzed arm to complete six different hand/wrist movements and benchmarked that performance to able-bodied individuals performing the same task.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A brain-computer interface (BCI) comprising:

a multichannel stimulator operatively connected to deliver stimulation pulses to a functional electrical stimulation (FES) device to control delivery of FES to an anatomical region; and a decoder operatively connected to receive at least one neural signal from at least one electrode operatively connected with a motor cortex and to control the multichannel stimulator based on the received at least one neural signal from the at least one electrode operatively connected with the motor cortex to cause the anatomical region to perform a predicted movement;

wherein the decoder comprises a computer programmed to process the received at least one neural signal from the at least one electrode operatively connected with the motor cortex using a deep neural network including an output neural network layer having units corresponding to a set of possible intended movements plus rest, wherein the deep neural network comprises a long short-term memory (LSTM) layer outputting to a convolutional layer in turn outputting to at least one fully connected neural network layer, and the convolutional layer is a one-dimensional convolutional layer that performs convolution in the time domain only, and wherein the unit with highest probability at a given time is the predicted movement or predicted rest for that given time.

2. The BCI of claim 1 wherein the LSTM layer includes hidden units that use a hard-sigmoid activation function and an output of the LSTM layer uses a hyperbolic tangent activation.

3. The BCI of claim 1, wherein the at least one fully connected neural network layer includes a fully connected neural network layer that uses a rectified linear unit activation function.

4. The BCI of claim 3 wherein the fully connected neural network layer outputs to the output neural network layer.

5. The BCI of claim 4 wherein the output neural network layer uses a softmax activation function scaling the outputs to correspond to probabilities.

6. The BCI of claim 1, wherein:
wherein an activation function for an output of the convolutional layer is a leaky-rectified linear unit; or
wherein the at least one fully connected neural network layer includes a fully connected neural network layer that uses a rectified linear unit activation function.

7. The BCI of claim 6, wherein the fully connected neural network layer outputs to the output neural network layer.

8. The BCI of claim 7 wherein the output neural network layer uses a softmax activation function scaling the outputs to correspond to probabilities.

9. The BCI of claim 1 wherein the unit of the output neural network layer of the decoder corresponding to rest implements a no-information decoder.

10. The BCI of claim 9 wherein the computer is programmed to process the received at least one neural signal also not using a boxcar filter.

11. An assistance device for assisting a patient having a spinal cord injury to manipulate an anatomical region that is paralyzed due to the spinal cord injury, the assistance device comprising:
a BCI as set forth in claim 1; and
a functional electrical stimulation (FES) device disposed on the anatomical region and including electrodes configured to deliver FES to the anatomical region;
wherein the multichannel stimulator of the BCI is operatively connected to deliver stimulation pulses to the FES device to control delivery of FES to the anatomical region.

12. An assistance method for assisting a patient having a spinal cord injury to manipulate an anatomical region of the patient that is paralyzed due to the spinal cord injury, the assistance method comprising:
applying a decoder to at least one neural signal received from at least one electrode operatively connected with a motor cortex of the patient to generate a predicted movement of the anatomical region, wherein the decoder comprises a computer programmed to process the at least one neural signal from the at least one electrode operatively connected with the motor cortex of the patient using a deep neural network to generate the predicted movement of the anatomical region by selecting the predicted movement from a set of possible intended movements plus rest, wherein the deep neural network comprises a long short-term memory (LSTM) layer outputting to a one-dimensional convolutional layer that performs convolution in the time domain only, in turn outputting to at least one fully connected neural network layer; and
performing functional electrical stimulation (FES) to cause the predicted movement of the anatomical region using a multichannel stimulator that is operatively connected to deliver stimulation pulses to a functional electrical stimulation (FES) device operatively connected to the anatomical region.

13. An assistance system comprising:
a brain-computer interface (BCI) comprising a computer operatively connected to receive at least one neural signal from a motor cortex of a patient and programmed to apply a decoder to the at least one neural signal from the motor cortex of the patient to generate a predicted movement, wherein the decoder comprises a deep neural network including an output neural network layer having units corresponding to a set of possible intended movements, wherein the unit with highest probability at a given time is the predicted movement for that given time; and
an assistive device, the BCI operatively connected to control the assistive device to perform the predictive movement;
wherein:
the deep neural network comprises a long short-term memory (LSTM) layer outputting to a convolutional layer in turn outputting to at least one fully connected neural network layer; and
the convolutional layer is a one-dimensional convolutional layer that performs convolution in the time domain only.

14. The assistance system of claim 13 wherein the assistive device comprises a functional electrical stimulation (FES) device, a robotic arm, a computer cursor, or a communication device.

15. The BCI of claim 1 wherein the one-dimensional convolutional layer performs convolution in the time domain only; or
wherein an activation function for an output of the one-dimensional convolutional layer is a leaky-rectified linear unit.

16. The assistance device of claim 11 further comprising:
at least one electrode operatively connected with a motor cortex of the patient;
wherein the decoder is operatively connected to receive the at least one neural signal from the at least one electrode operatively connected with the motor cortex of the patient.

17. The BCI of claim 1 wherein rest comprises the anatomical region remaining in a neutral resting position.

* * * * *